(12) United States Patent
Asogawa et al.

(10) Patent No.: US 8,623,294 B2
(45) Date of Patent: Jan. 7, 2014

(54) FLOW PASSAGE CONTROL MECHANISM FOR MICROCHIP

(75) Inventors: Minoru Asogawa, Tokyo (JP); Hisashi Hagiwara, Kanagawa (JP); Tohru Hiramatsu, Nagano (JP)

(73) Assignee: NEC Corporation, Tokyo (JP)

( * ) Notice: Subject to any disclaimer, the term of this patent is extended or adjusted under 35 U.S.C. 154(b) by 15 days.

(21) Appl. No.: 12/920,256

(22) PCT Filed: Mar. 18, 2009

(86) PCT No.: PCT/JP2009/056025
§ 371 (c)(1),
(2), (4) Date: Aug. 30, 2010

(87) PCT Pub. No.: WO2009/119698
PCT Pub. Date: Oct. 1, 2009

(65) Prior Publication Data
US 2011/0000561 A1 Jan. 6, 2011

(30) Foreign Application Priority Data
Mar. 24, 2008 (JP) ................. 2008-075395

(51) Int. Cl.
*G01N 15/06* (2006.01)
(52) U.S. Cl.
USPC ............ 422/502; 422/50; 422/68.1; 422/503; 422/509; 436/43; 436/180
(58) Field of Classification Search
USPC ............. 422/50, 68.1, 502, 503, 504; 436/43, 436/68.1
See application file for complete search history.

(56) References Cited

U.S. PATENT DOCUMENTS

| 5,593,130 A | 1/1997 | Hansson et al. |
| 8,178,056 B2 | 5/2012 | Yokoyama |
| 2001/0029983 A1* | 10/2001 | Unger et al. ................. 137/597 |
| 2005/0284213 A1* | 12/2005 | Karp et al. ................... 73/61.52 |

(Continued)

FOREIGN PATENT DOCUMENTS

| CA | 2 656 686 A1 | 1/2008 |
| CN | 1168720 A | 12/1997 |

(Continued)

OTHER PUBLICATIONS

Office Action, dated Feb. 6, 2013, issued by the Japanese Patent Office in counterpart Japanese Patent Application No. 2010-505745.

*Primary Examiner* — Brian J Sines
(74) *Attorney, Agent, or Firm* — Sughrue Mion, PLLC

(57) ABSTRACT

A channel control mechanism for a microchip has a laminated structure formed of members including elastic members, and includes: a sample reservoir for packing a sample therein; a reaction reservoir in which mixture and reaction of the sample are performed; and a channel formed in a middle layer of the laminated structure, for bringing the sample reservoir and the reaction reservoir into communication with each other. The channel control mechanism performs the reaction and analysis in such a manner that the sample is delivered into the reaction reservoir through the channel. A shutter channel (pressurizing channel) is provided in a layer different from a layer in which the channel is formed so that the pressurizing channel partially overlaps the channel. The channel is closed through applying a pressurized medium to the shutter channel (pressurizing channel), and the channel is opened through releasing a pressure of the pressurized medium.

9 Claims, 17 Drawing Sheets

(56) References Cited

U.S. PATENT DOCUMENTS

| | | |
|---|---|---|
| 2006/0088929 A1 | 4/2006 | Nakajima et al. |
| 2006/0093517 A1 | 5/2006 | Yokoyama |
| 2006/0160243 A1 | 7/2006 | Tang et al. |
| 2006/0252087 A1 | 11/2006 | Tang et al. |
| 2008/0057274 A1 | 3/2008 | Hagiwara et al. |

FOREIGN PATENT DOCUMENTS

| | | |
|---|---|---|
| CN | 1369039 A | 9/2002 |
| JP | 9-502249 A | 3/1997 |
| JP | 3746207 B2 | 11/2002 |
| JP | 2003-107094 A | 4/2003 |
| JP | 2003-212152 A | 7/2003 |
| JP | 2004-291187 A | 10/2004 |
| JP | 2005-308200 A | 11/2005 |
| JP | 2006-132965 A | 5/2006 |
| JP | 2007-101200 A | 4/2007 |
| JP | 2007-309868 A | 11/2007 |
| WO | 95/07425 A1 | 3/1995 |
| WO | 2006/046433 A1 | 5/2006 |
| WO | 2006/078470 A2 | 7/2006 |
| WO | 2008/004572 A1 | 1/2008 |

* cited by examiner

FLOW PASSAGE CONTROL MECHANISM FOR MICROCHIP

TECHNICAL FIELD

This invention relates to a channel control mechanism for an analysis microchip (microchip), which includes a plurality of sample reservoirs and a reaction reservoir used for gene analysis and the like, and in which the reaction reservoir and the sample reservoirs are continuous with each other through a micro channel.

BACKGROUND ART

In recent years, for a chip which includes a packing vessel and a micro channel on one chip, and is referred to as a microchip, a lab-on-chip, a microreactor, a fluidic chip, or a chemical reaction cartridge, there have been studied various delivering mechanisms and methods for controlling and delivering a sample or a liquid sample to allow the sample or the liquid sample to react, to thereby perform analysis of micro components such as gene. As technologies relating to the mechanisms and methods, there are disclosed, for example, Japanese Unexamined Patent Application Publication (JP-A) No. 2003-212152 (Patent Document 1), Japanese Patent No. 3746207 (Patent Document 2), Japanese Unexamined Patent Application Publication (JP-A) No. 2005-308200 (Patent Document 3), and Japanese Unexamined Patent Application Publication (JP-A) No. 2007-101200 (Patent Document 4).

According to Patent Document 1, in "a substrate which is formed of an elastic body and includes a micro channel in an inside thereof", the following structure is adopted as delivering means. Specifically, "the micro channel is pressed through applying a mechanical pressure onto the substrate by a gear-shaped roller. Then, through rotating the roller while applying the pressure thereon, a periodic pressure is applied onto the substrate, and thus a fluid is moved."

According to Patent Document 2, in "a sheet-type microreactor", the following structure is adopted as delivering means. Specifically, "rotary drive means performs rotation for applying a centrifugal force to a specimen, and moving means moves the centrifugally separated specimen from the second gap part to the third gap part."

According to Patent Document 3, in "a fluidic chip in which a part of an upper portion of a micro channel is formed of an elastic member", the following structure is adopted as deliver opening/closing means. Specifically, "a micro-valve mechanism includes a pressure control port erected on the elastic member on the fluidic chip, and opens/closes a valve by applying/releasing a pressure via the pressure control port."

According to Patent Document 4, in "a chemical reaction cartridge" having a laminated structure including an elastic member, the following structure is adopted as delivering means or opening/closing means. Specifically, "the chemical reaction cartridge causes deformation to occur upon application of an external force, and transfers or seals substances contained therein."

In addition, "Solving means" section in Abstract and "Embodiments of the Invention" section, the structure in which "a roller is rotated while kept pressed into contact with the cartridge" is described.

DISCLOSURE OF THE INVENTION

Problems to be Solved by the Invention

However, in the conventional technology regarding delivering disclosed in Patent Document 1, when delivering a sample into a reaction reservoir serving as a sample-delivered side through the channel from a sample reservoir provided on the chip to serves as a sample-delivering side, delivering is performed while crushing the channel by the gear-shaped roller. Thus, the sample remains in the channel, and it is impossible to completely deliver the sample remaining in the channel just before the reaction reservoir serving as the delivered side. In addition, in the reaction reservoir as the delivered side, steps of sequentially delivering, mixing, and disposing of a plurality of samples are generally performed. Thus, the sample previously delivered is not completely disposed of from the channel or the reaction reservoir so that a micro amount of the sample remains, which may adversely affect the sample to be delivered in the subsequent step.

Further, complex control means is required to control and drive the gear-shaped roller, and a function of the delivering means depends on a press-contact force of the roller itself pressing the chip. Thus, in the case where a plurality of opening/closing mechanisms are required, a large number of rollers are required, and the sample reservoir and the reaction reservoir serving as a packing side and a packed side are restricted in position. In addition, there is a problem in that the mechanism structure is increased in size, complicated, and high-priced.

Further, it is impossible to completely discharge and control the sample remaining in the channel just before the sample reservoir and the reaction reservoir serving as the packing side and the packed side and being continuous with the channel, and hence a micro amount of the sample remains and is mixed with the sample to be used in the subsequent step. As a result, there is a problem in that contamination occurs and adversely affects reliability of analysis results.

Further, in the conventional technology regarding delivering disclosed in Patent Document 2, the following structure is adopted. Specifically, the microreactor itself including a plurality of channels and a plurality of gaps for a sample is mounted to a centrifugal separator, and the sample packed in the gap by a centrifugal force is delivered into another gap through the channels. With this structure, the centrifugal separator is needed as the delivering means, and hence the device structure is complicated, increased in size, and high-priced. Further, only a structure including a single channel and a single gap can be formed in a delivering direction, in other words, there is a problem in that it is impossible to deliver the sample into the plurality of gaps stepwise.

Further, in the conventional technology regarding opening/closing of the channel disclosed in Patent Document 3, a pressing body is brought into press-contact with the channel provided inside the chip from an upper surface of the fluidic chip formed of the elastic member, to thereby close the channel. Further, the channel is opened along with releasing the pressure. However, in the case of sequentially delivering a plurality of samples, it is impossible to remove the sample remaining in the channel other than a valve portion. As a result, there is a problem in that the remaining sample adversely affects the sample to be delivered in the subsequent step and affects reliability.

Further, in the conventional technology regarding delivering disclosed in Patent Document 4, a roller-like pressing body is brought into press-contact with the channel provided inside the chip from an upper surface of the cartridge formed of the elastic member, and the roller is moved while crushing the channel, to thereby deliver the samples remaining in the vessel and the channel. However, in the case of delivering the samples into the reaction reservoir serving as the sample-delivered side through the channel from the sample reservoir provided on the chip to serves as the sample-delivering side, when the roller completely crushes the channel, it is impossible to completely discharge the samples remaining in the channels just before the sample reservoir and the reaction reservoir due to capillary phenomenon caused by surface tension of the sample. As a result, there are problems in that the sample remains in the channel, and that it is impossible to completely deliver the sample remaining in the channel just before the reaction reservoir serving as the delivered side.

Further, in the reaction reservoir as the delivered side, steps of delivering, mixing, and disposing of a plurality of samples are generally performed. Accordingly, when the sample previously delivered is not completely disposed of, there is a problem in that the sample to be delivered later is adversely affected. Still further, in the case where a plurality of opening/closing mechanisms are required, a large number of rollers are required, and the sample reservoir and the reaction reservoir serving as the packing side and the packed side are restricted in position. In addition, there is a problem in that the mechanism structure is increased in size, complicated, and high-priced.

This invention has been made in view of the problems of the above-mentioned conventional technologies, and therefore it is an object of this invention to provide a channel control mechanism which uses a simple mechanism, and in which, in order to prevent mutual contamination during delivering, no sample remains even just before a delivered-side vessel and no sample remains in the channel during discharge of liquid.

Means to Solve the Problems

In order to achieve the above-mentioned object, according to this invention, a channel control mechanism for a microchip having a laminated structure formed of members including elastic members, includes: a sample reservoir for packing a sample therein; a reaction reservoir in which mixture and reaction of the sample are performed; and a channel formed in a middle layer of the laminated structure, for bringing the sample reservoir and the reaction reservoir into communication with each other, the channel control mechanism performing the reaction and analysis in such a manner that the sample is delivered into the reaction reservoir through the channel, in which: a pressurizing channel is provided in a layer different from a layer in which the channel is formed so that the pressurizing channel partially overlaps the channel; the channel is closed through applying a pressurized medium to the pressurizing channel; and the channel is opened through releasing a pressure of the pressurized medium.

Further, according to this invention, there is provided a channel control mechanism for a microchip for performing reaction and analysis of a sample, the microchip including: a first member which has a laminated structure formed of members including stretchable members, and includes: a sample reservoir for packing the sample therein; a reaction reservoir in which mixture and the reaction of the sample are performed; and a channel formed in a middle layer of the laminated structure, for bringing the sample reservoir and the reaction reservoir into communication with each other, the first member performing the reaction and the analysis in such a manner that the sample is delivered into the reaction reservoir through the channel; and a second member which has a laminated structure formed of members including stretchable members, and includes a pressurizing channel, in which: the pressurizing channel partially overlaps the channel when the first member and the second member are superimposed on each other; the channel is closed through applying a pressurized medium to the pressurizing channel; and the channel is opened through releasing a pressure of the pressurized medium.

Effect of the Invention

According to this invention, there is structured a closing mechanism in which the pressurizing channel crushes the channel from a layer near the channel formed in the elastic members, and hence it is possible to reliably block the channel.

BEST MODE FOR EMBODYING THE INVENTION

Next, embodiments of this invention are described with reference to the drawings.

Figure 1:
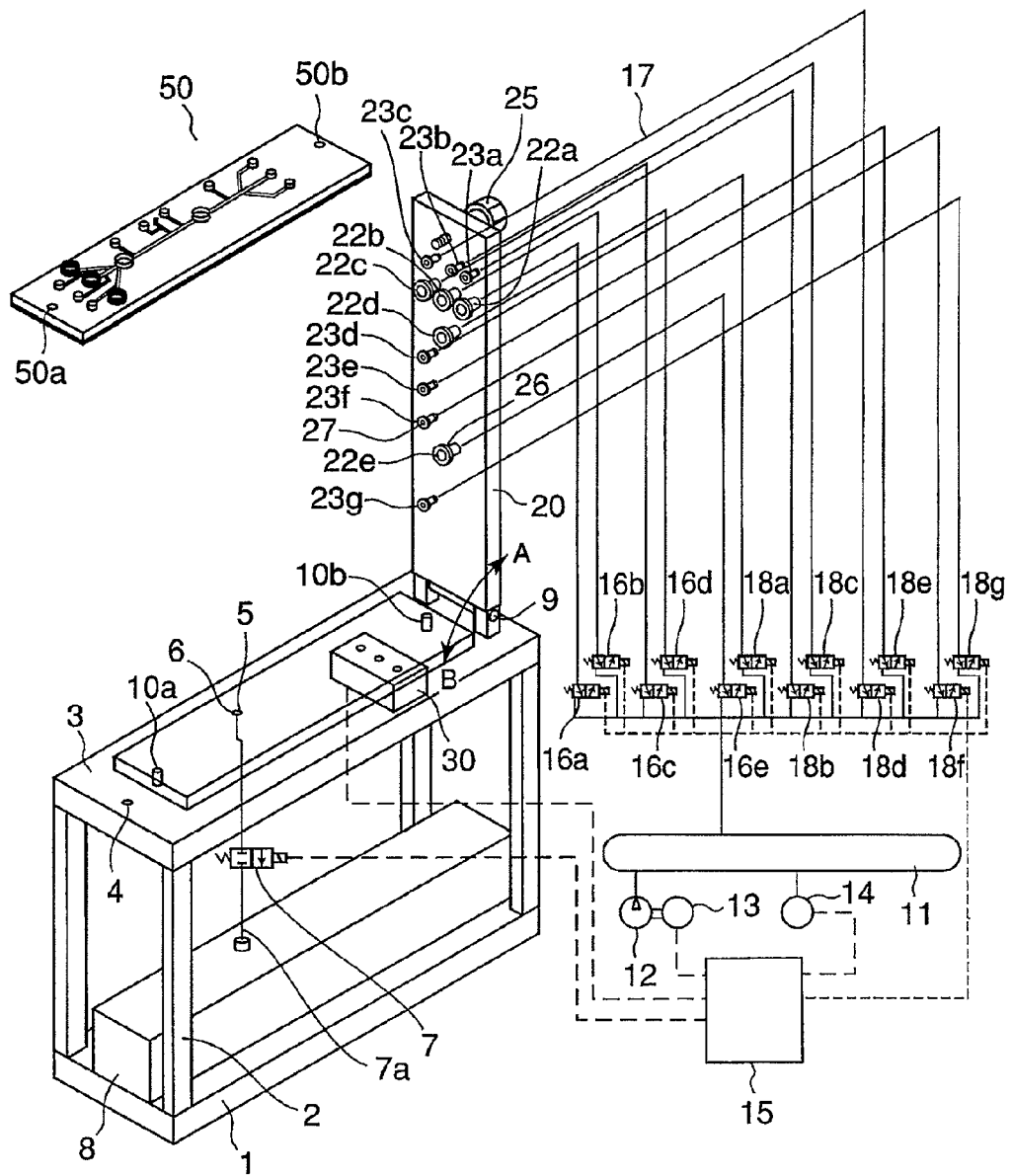
FIG. 1 is a sectional perspective view illustrating a structure of a delivering device for a microchip used in this invention.

FIG. 1 is a perspective view illustrating a structure of a device which delivers a sample and causes the sample to react using a microchip and a delivering method according to this invention, to thereby perform analysis of micro components such as gene analysis.

On a machine casing 1, a table 3 is provided through poles 2. Further, in a table 3, a disposal hole 5 whose periphery is sealed by an O-ring 6 is provided. Further, the disposal hole 5 is connected to a disposal reservoir 8 provided onto the machine casing 1 through a disposal solenoid-controlled valve 7 and a tube 7a. Further, in an upper surface of the table 3, positioning pins 10a and 10b corresponding to pin holes 50a and 50b provided in a microchip 50 to serve as a guide to a predetermined position are provided in a protruding manner. Further, on the table 3, through a hinge 9, there is provided, so as to be rotatable to the directions A and B, a cover 20 having a fastening screw 25, pressurizing holes 22a, 22b, 22c, 22d, and 22e which pass through the cover 20 and is sealed by an O-ring 26 from the peripheries thereof, shutter pressurizing holes 23a, 23b, 23c, 23d, 23e, 23f, and 23g sealed by O-ring 27 from the peripheries thereof. Further, in one end on the table 3, a screw hole 4 is provided at a position corresponding to the fastening screw 25.

Further, the pressurizing holes 22a, 22b, 22c, 22d, and 22e which are provided while passing through the cover 20 are connected to secondary sides of pressurizing solenoid-controlled valves 16a, 16b, 16c, 16d, and 16e through tubes 17. Further, shutter pressurizing holes 23a, 23b, 23c, 23d, 23e, 23f, and 23g are connected to secondary sides of shutter solenoid-controlled valves 18a, 18b, 18c, 18d, 18e, 18f, and 18g. Further, primary sides of the pressurizing solenoid-controlled valves 16a, 16b, 16c, 16d, and 16e, and the shutter solenoid-controlled valves 18a, 18b, 18c, 18d, 18e, 18f, and 18g are connected to a pressure accumulator 11. To the pressure accumulator 11, a pump 12 driven by a motor 13 and a pressure sensor 14 for detecting inner pressure are connected.

Meanwhile, to a controller 15 for executing a predetermined program, there are connected, so as to be capable of being operationally controlled, the pressurizing solenoid-controlled valves 16a, 16b, 16c, 16d, and 16e, the disposal solenoid-controlled valve 7, and the shutter solenoid-controlled valves 18a, 18b, 18c, 18d, 18e, 18f, and 18g. Further, the motor 13 and the pressure sensor 14 are connected, the motor 13 driving the pump 12 so as to control the pressure in the pressure accumulator 11 to a predetermined pressure, and the pressure sensor 14 detecting the pressure in the pressure accumulator 11 to perform feedback. With the above-mentioned structure, due to instructions from the controller 15, the pressure in the pressure accumulator 11 is constantly kept in a predetermined pressure.

Figure 2:
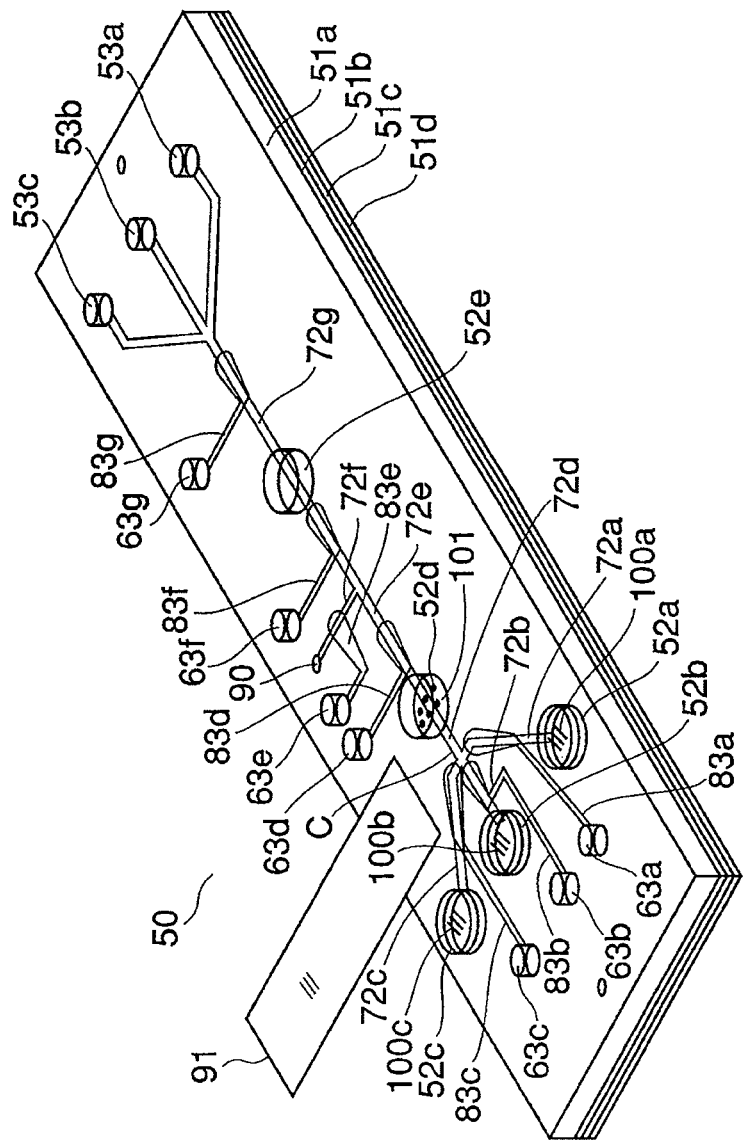
FIG. 2 is a perspective view illustrating a mechanism structure of the microchip according to this invention.

FIG. 2 is a perspective view illustrating details of the microchip 50 according to an embodiment of this invention.

The microchip 50 has a multi-layer structure, in which a main plate 51a, a second plate 51b (sheet), a third plate 51c (sheet), and a fourth plate 51d (sheet), each being made of a flexible resin, are laminated together.

On the microchip 50, there are provided sample reservoirs 52a, 52b, and 52c and second reaction reservoirs 53a, 53b, and 53c which pass through the main plate 51a and the second plate 51b to be formed into recessed shapes. In addition, there are provided a reaction reservoir 52d and an extraction reservoir 52e which pass through the main plate 51a and the fourth plate 51d and surround the second plate 51b and the third plate 51c while not passing through the second plate 51b and the third plate 51c. Further, an adsorption member 101, which is represented by magnetic beads absorbing micro components, is dry-fixed in the reaction reservoir 52d. Note that, dry-fixing is described below with reference to FIG. 4.

Further, on the microchip 50, there are provided shutter ports 63a, 63b, 63c, 63d, 63e, 63f, and 63g which pass through the main plate 51a, the second plate 51b, and the third plate 51c to be formed into recessed shapes. Further, there is provided a disposal hole 90 which passes through the second plate 51b, the third plate 51c, and the fourth plate 51d to a downward direction.

Further, when the microchip 50 is installed on the table 3 illustrated in FIG. 1, and the cover 20 is rotated to a B direction, to thereby sandwich the microchip 50 between the table 3 and the cover 20 by the fastening screw 25 and the screw hole 4, the sample reservoirs 52a, 52b, and 52c, the reaction reservoir 52d, the extraction reservoir 52e, and the shutter ports 63a, 63b, 63c, 63d, 63e, 63f, and 63g are installed at positions corresponding to the pressurizing holes 22a, 22b, and 22c, the pressurizing hole 22d, the pressurizing hole 22e, and the shutter pressurizing holes 23a, 23b, 23c, 23d, 23e, 23f, and 23g, respectively.

Further, the sample reservoirs 52a, 52b, and 52c, the reaction reservoir 52d, the extraction reservoirs 52e, the second reaction reservoir 53a, 53b, and 53c are continuous with each other through channels 72a, 72b, 72c, 72d, 72e, 72f, and 72g formed between the second plate 51b and the third plate 51c. Further, the shutter ports 63a, 63b, 63c, 63d, 63e, 63f, and 63g are continuous with shutter channels (pressurizing channels) 83a, 83b, 83c, 83d, 83e, 83f, and 83g, respectively, which are formed between the third plate 51c and the fourth plate 51d. Further, leading ends of the shutter channels extend to below the channels 72a, 72b, 72c, 72d, 72e, 72f, and 72g through the third plate 51c, and are provided so as to partially intersect the channels 72a, 72b, 72c, 72d, 72e, 72f, and 72g.

Further, the channels 72a, 72b, 72c, 72d, 72e, 72f, and 72g are formed by, when the second plate 51b and the third plate 51c constituting the channels are bonded to each other, non-bonded portions for the channels and by keeping a separable state thereof. Similarly, the shutter channels 83a, 83b, 83c, 83d, 83e, 83f, and 83g are formed by, when the third plate 51c and the fourth plate 51d constituting the shutter channels are bonded to each other, non-bonded portions for the channels and by keeping the separable state thereof.

Further, similarly, portions situated between the second plate 51b and the third plate 51c in the reaction reservoir 52d and the extraction reservoir 52e have substantially the same diameter as that of a through-hole of the main plate 51a, and are not subjected to bonding, to thereby be continuous with the channels 72d, 72e, and 72g. Moreover, when a sample is injected in an inside of each of the portions, the portion having the same diameter is swelled to accumulate the sample.

In addition, after samples 100a, 100b, and 100c are packed in the sample reservoirs 52a, 52b, and 52c, respectively, a film 91 formed of an elastic member is placed to cover the sample reservoirs 52a, 52b, and 52c entirely.

An operation of delivering from the sample reservoirs 52a, 52b, and 52c is described with reference to FIG. 3. FIGS. 3A and 3B are sectional views of the sample reservoirs 52a, 52b, and 52c.

Figure 3A:
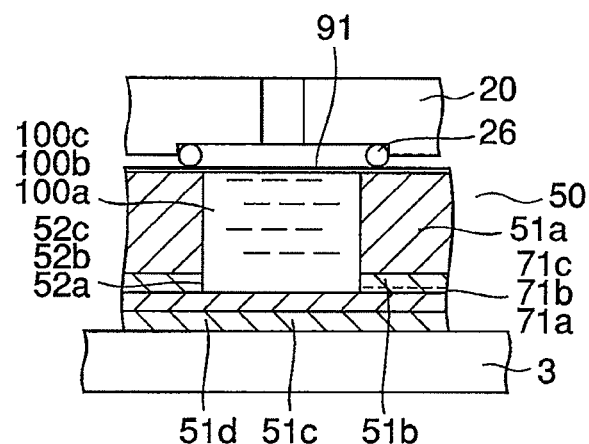
FIGS. 3A and 3B are sectional views illustrating an operating state of the microchip according to this invention.
Figure 3B:
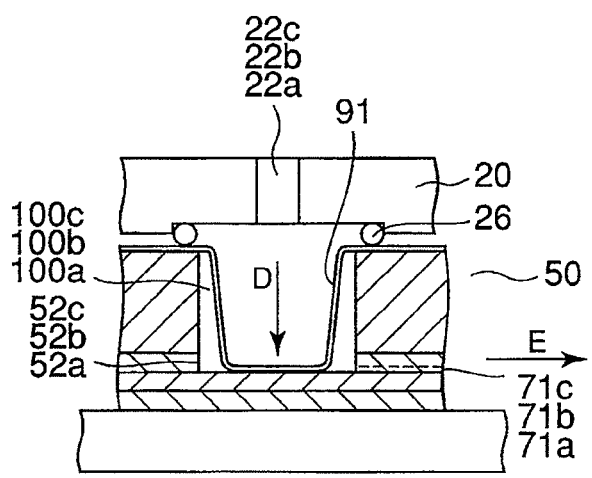

FIG. 3A illustrates an initial state in which the samples 100a, 100b, and 100c are respectively packed in the sample reservoirs 52a, 52b, and 52c passing through the main plate 51a and the second plate 51b of the microchip 50 and upper portions of the reservoirs are sealed with the film 91. Moreover, the microchip 50 is sandwiched between the cover 20 and the table 3 through the O-rings 26. Further, between the second plate 51b and the third plate 51c formed of elastic members constituting the microchip 50, channels 71a, 71b, and 71c formed of non-bonded portions are continuous with the sample reservoirs 52a, 52b, and 52c. For convenience of description, each of the channels 71a, 71b, and 71c is illustrated by a broken line in the figures as a solid portion with a volume. However, in actual fact, the channels 71a, 71b, and 71c are formed of the non-bonded portions in a closed state.

Next, a delivering operation is described with reference to FIG. 3B. When the pressurizing solenoid-controlled valves 16a, 16b, and 16c are turned ON from the state illustrated in FIG. 3B based on a previously-set program of the controller 15 illustrated in FIG. 1, a pressurized medium represented by the compressed air is applied to the pressurizing ports 22a, 22b, and 22c of the cover 20. As a result, because peripheries of the pressurizing holes 22a, 22b, and 22c are sealed with the O-rings 26, the pressurized medium, which is applied from the pressurizing ports 22a, 22b, and 22c formed in the cover 20 illustrated in FIG. 3B, pushes the film 91 formed of the elastic member in a D direction, that is, into insides of the sample reservoirs 52a, 52b, and 52c, to thereby pressurize the packed samples 100a, 100b, and 100c. In addition, the pressurized samples 100a, 100b, and 100c flow out in an E direction while expanding the channels 71a, 71b, and 71c which are opened on the program and are formed between the second plate 51b and the third plate 51c.

Figure 4A:
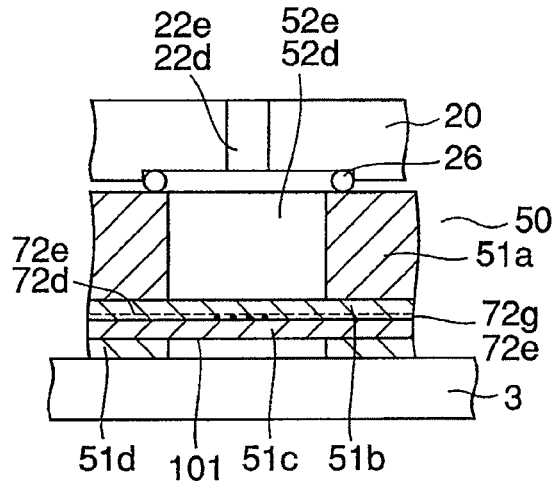
FIGS. 4A to 4C are sectional views illustrating an operating state of the microchip according to this invention.

Next, a delivering operation to the reaction reservoir 52d and the extraction reservoir 52e and an extraction operation are described with reference to FIG. 4. FIG. 4A is a sectional view illustrating a state before injection to the reaction reservoir 52d and the extraction reservoir 52e.

The microchip 50 is sandwiched between the O-rings 26 of the cover 20 and the table 3. In the reaction reservoir 52d and the extraction reservoir 52e, the main plate 51a and the fourth plate 51d constituting the microchip 50 are in the form of the through-hole, and each of the second plate 51b and the third plate 51c surrounded in middle portions includes the non-bonded portion having substantially the same diameter as that of each of the reaction reservoir 52d and the extraction reservoir 52e. In addition, each end of the non-bonded portion is continuous with the channels 72d and 72e, or the channels 72e and 72g. Further, the adsorption member 101 is dry-fixed in the inside of the reaction reservoir 52d.

Next, a flowing-out operation from the reaction reservoir 52d and the extraction reservoir 52e is described with reference to FIG. 4B.

As illustrated in FIG. 3, the samples 100a, 100b, and 100c are delivered into the channels 72d and 72e from the E direction. In addition, based on the previously-set program, the channels 72e and 72g on an outflow side are closed, and a pressure of the pressurized medium represented by the air is released with respect to the pressurizing ports 22d and 22e. As a result, while swelling the second plate 51b and the third plate 51c into a balloon shape, the samples 100a, 100b, and 100c are delivered into the non-bonded portions which are formed of the second plate 51b and the third plate 51c and have the same diameter as that of each of the reaction reservoir 52d and the extraction reservoir 52e.

Next, a delivering operation from the reaction reservoir 52d and the extraction reservoir 52e is described with reference to FIG. 4C.

Figure 4B:
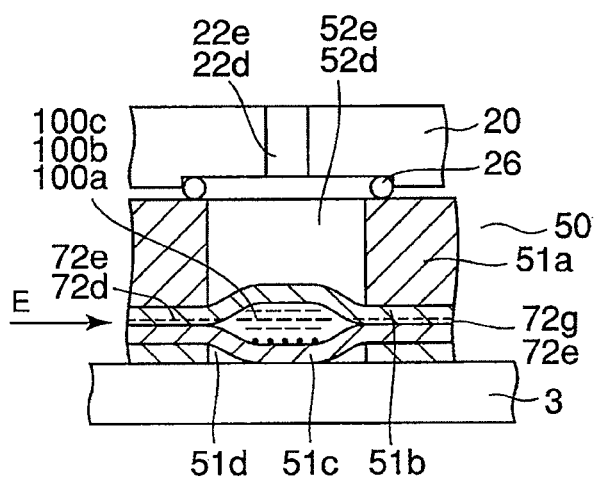
Figure 4C:
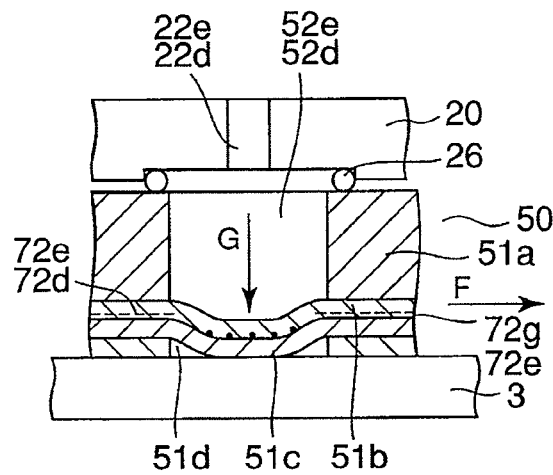

When the pressurized medium represented by the air is applied from the pressurizing ports 22d and 22e in the cover 20 from the above-mentioned state illustrated in FIG. 4B, and the inflow channels 72d and 72e are closed and the outflow channels 72e and 72g are opened, the samples 100a, 100b, and 100c packed in the non-bonded portions of the second plate 51b and the third plate 51c swelled into a balloon shape are pressurized, to thereby be discharged in an F direction through the outflow channels 72e and 72g.

With the above-mentioned structure, based on the previously-set program in the controller 15, the pressure of the pressurized medium represented by the air inside the pressure accumulator 11 is sequentially applied to the pressurizing holes 22a, 22b, 22c, 22d, and 22e and the shutter pressurizing holes 23a, 23b, 23c, 23d, 23e, 23f, and 23g of the cover 20 through the pressurizing solenoid-controlled valves 16a, 16b, 16c, 16d, and 16e, the disposal solenoid-controlled valve 7, and the shutter solenoid-controlled valves 18a, 18b, 18c, 18d, 18e, 18f, and 18g.

As a result, in the microchip 50, the pressure of the pressurized medium represented by the air is sequentially applied to upper portions of the sample reservoirs 52a, 52b, and 52c, the reaction reservoir 52d, and the extraction reservoir 52e based on a program operation. In addition, similarly, the pressurized medium represented by the air is sequentially applied to the shutter ports 63a, 63b, 63c, 63d, 63e, 63f, and 63g based on the program operation. In other words, through opening/closing desired channels and through applying the pressurized medium to the upper portions of the sample reservoirs 52a, 52b, and 52c, the reaction reservoir 52d, and the extraction reservoir 52e based on the program, it is possible to deliver the samples 100a, 100b, and 100c into the reaction reservoir 52d, the extraction reservoir 52e, and the second reaction reservoirs 53a, 53b, and 53c, and to dispose of the samples to the outside through the disposal hole 90.

Next, a detailed structure and a detailed operation of the microchip according to this invention are described with reference to FIGS. 5 to 20. Here, FIGS. 5 to 20 are plan views illustrating a part of the microchip. Note that, for convenience of description, the channels are illustrated by solid lines, and the shutter channels are illustrated by broken lines.

Figure 5:
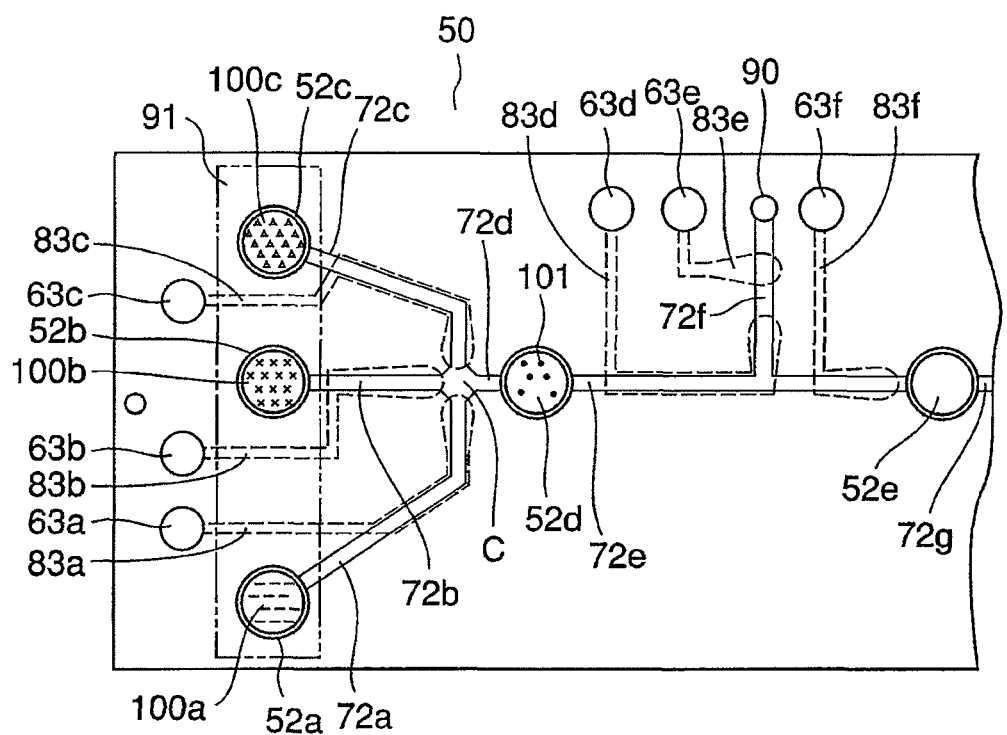
FIG. 5 is a plan view illustrating details of a part of the microchip according to an embodiment of this invention.

FIG. 5 illustrates an initial state of the microchip 50. As illustrated in FIG. 3A, the sample reservoirs 52a, 52b, and 52c on the microchip 50 are packed with the samples 100a, 100b, and 100c, respectively, and the upper portions of the sample reservoirs are covered with the film 91 formed of the elastic member. As illustrated in FIG. 4, each of the reaction reservoir 52d and the extraction reservoir 52e is in the form of a balloon, and the adsorption member 101 absorbing micro components is fixed in the reaction reservoir 52d.

Further, the sample reservoirs 52a, 52b, and 52c are continuous with the reaction reservoir 52d by the channels 72a, 72b, 72c, and 72d through an intersecting portion C having a part of a common region. Further, the reaction reservoir 52d is continuous with the extraction reservoir 52e and the disposal hole 90 under a state in which the channels 72e and 72f are branched.

Still further, the shutter channels 83a, 83b, and 83c are continuous with the shutter ports 63a, 63b, and 63c, respectively. As illustrated in FIG. 2, one end of each of the shutter channels 83a, 83b, and 83c extends to below the channel 72a, 72b, or 72c, and is provided while overlapping a part of the common region at the intersecting portion C. In addition, the U-shaped shutter channel 83d is continuous with the shutter port 63d, and one end of the shutter channel 83d extends to below the channels 72e and 72f in an overlapping state to reach a halfway point of the channel 72f.

Moreover, the shutter channel 83e is continuous with the shutter port 63e, and one end of the shutter channel 83e extends to below the channel 72f to extend to between a vicinity of a trailing end of the shutter channel 83d and the disposal hole 90. Further, the shutter channel 83f is continuous with the shutter port 63f, and one end of the shutter channel 83f extends to below the channel 72e in an overlapping state to extend to a vicinity of the extraction reservoir 52e. Further, the channel 72g is continuous with the extraction reservoir 52e, and is continuous with the second reaction reservoirs 53a, 53b, and 53c illustrated in FIG. 2.

In an initial stage illustrated in FIG. 5, based on an instruction from the controller 15 which is illustrated in FIG. 1 and executes the program, the pressurized medium is not applied to the pressurizing holes 22a, 22b, 22c, 22d, and 22e and the shutter pressurizing holes 23a, 23b, 23c, 23d, 23e, 23f, and 23g. In other words, the pressurized medium is not applied to the upper portions of the sample reservoirs 52a, 52b, and 52c, the reaction reservoir 52d, and the extraction reservoir 52e and the shutter ports 63a, 63b, 63c, 63d, 63e, 63f, and 63g of the microchip 50 illustrated in FIG. 5.

Next, an operation in a first stage is described with reference to FIG. 6. The operation in the first stage is a step of delivering the sample 100a packed in the sample reservoir 52a into the reaction reservoir 52d. From the initial stage illustrated in FIG. 5, the pressurized medium is applied to the shutter ports 63b, 63c, 63d, 63e, and 63f. As a result, the pressurized medium is guided to the shutter channels 83b, 83c, 83d, 83e, and 83f to deform the elastic member, to thereby close the channels 72b, 72c, 72e, and 72f. Then, when being applied with the pressurized medium from the upper portion of the sample reservoir 52a, the inside sample 100a is delivered through the film 91 as illustrated in FIG. 3. At this time, as illustrated in FIG. 4, the sample 100a is delivered in a G direction, that is, into the reaction reservoir 52d through the channel 72a which is exclusively opened.

Next, an operation in a second stage is described with reference to FIG. 7. The operation in the second stage is a step of delivering, into the reaction reservoir 52a, the sample 100a delivered into the channel 72a to remain therein. When the pressurized medium is applied to the shutter port 63a from the state illustrated in FIG. 6, the pressurized medium is guided to the shutter channel 83a to be guided to below the channel 72a, and deforms the elastic member, to thereby squeeze, in the G direction, the sample 100a remaining in the portion of the channel 72a overlapping the shutter channel 83a. As a result, the sample 100a remaining in the channel 72a is further packed in the reaction reservoir 52d. Meanwhile, in the reaction reservoir 52d, micro components contained in the sample 100a come into contact with the adsorption member 101 to be absorbed.

Figure 7:
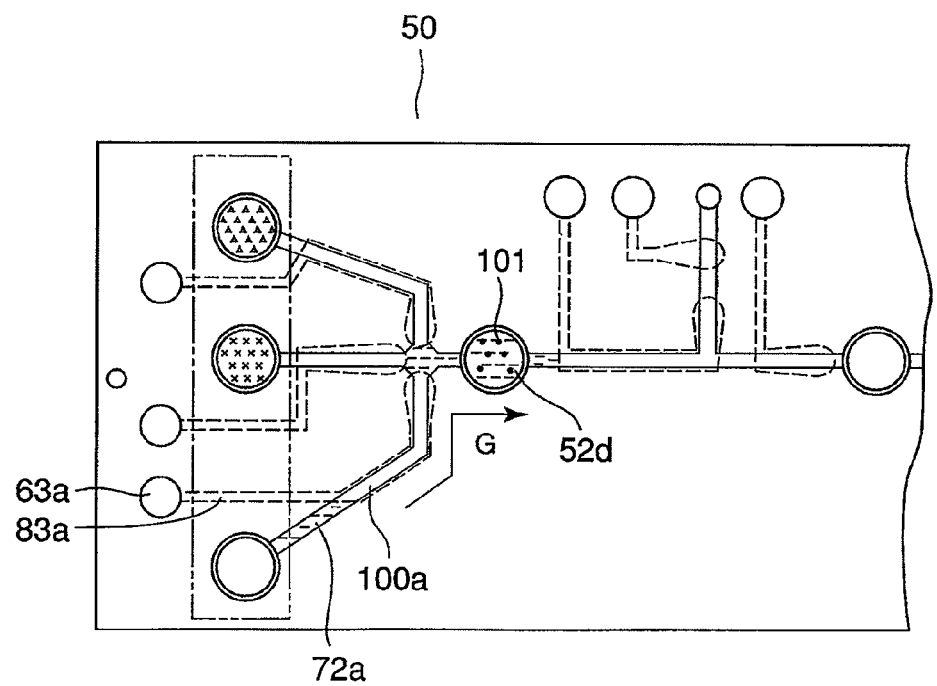
FIG. 7 is a plan view illustrating an operation of the microchip according to the embodiment of this invention.
Figure 8:
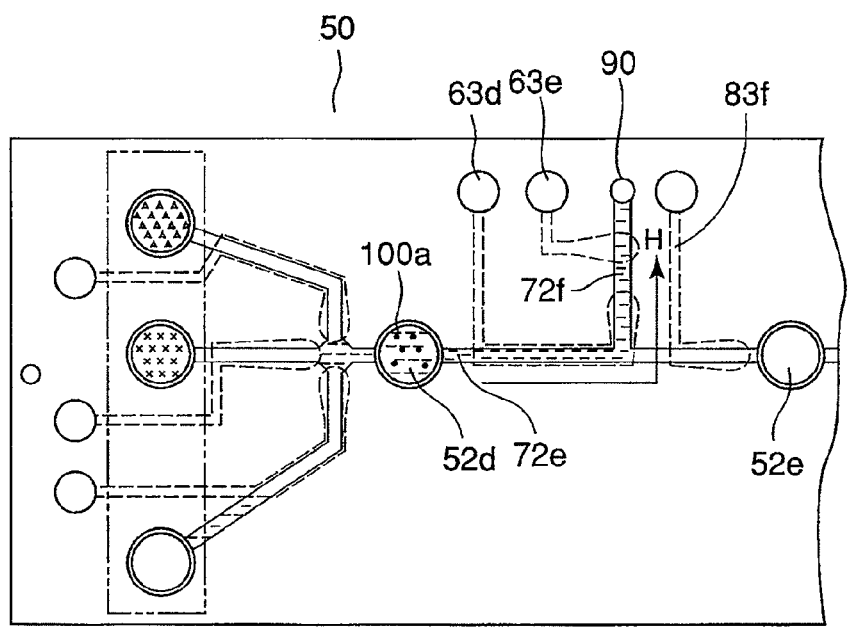
FIG. 8 is a plan view illustrating an operation of the microchip according to the embodiment of this invention.

Next, an operation in a third stage is described with reference to FIG. 8. The operation in the third stage is a step of disposing of the sample 100a packed in the reaction reservoir 52d. After canceling application of the pressurized medium applied to the shutter ports 63d and 63e from the state of the second stage illustrated in FIG. 7, the pressurized medium is applied from the upper portion of the reaction reservoir 52d. As a result, the channels 72e and 72f are opened. Further, the inflow channel into the extraction reservoir 52e has been already closed by the shutter channel 83f. In addition, as illustrated in FIG. 4, the sample 100a packed in the reaction reservoir 52a is delivered into the channels 72e and 72f which are exclusively opened, that is, in an H direction, and hence the sample 100a is disposed of through the disposal hole 90.

Figure 9:
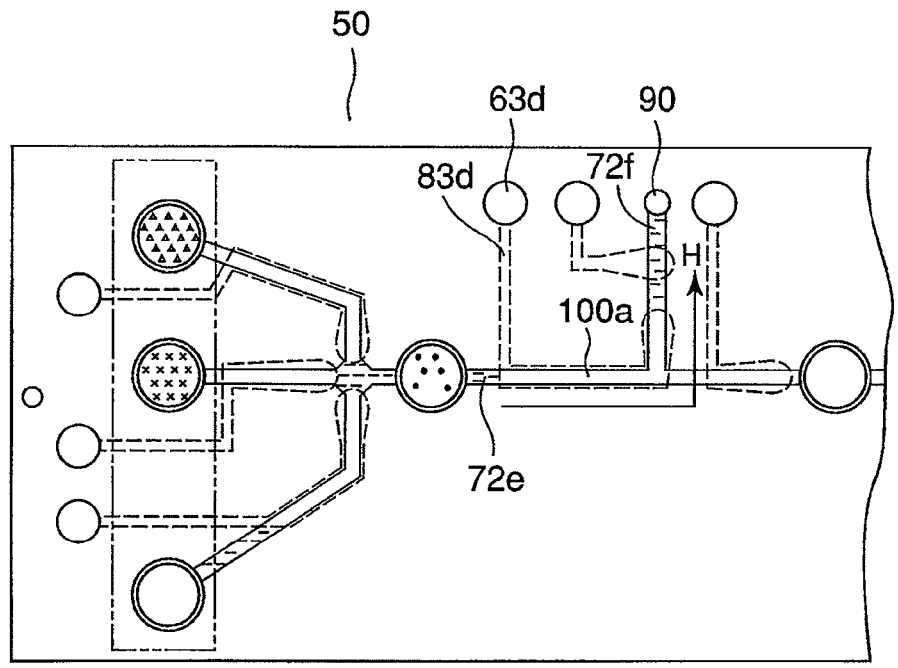
FIG. 9 is a plan view illustrating an operation of the microchip according to the embodiment of this invention.

Next, an operation in a fourth stage is described with reference to FIG. 9. The operation in the fourth stage is a step of disposing of the sample 100a which is delivered into parts of the channels 72e and 72f to remain therein. When the pressurized medium is applied to the shutter port 63d from the state of the third stage illustrated in FIG. 8, the pressurized medium is guided to the shutter channel 83d, to thereby squeeze and dispose of the sample 100a remaining in the portions of the channels 72e and 72f overlapping the shutter channel 83d in the H direction, that is, toward the disposal hole 90.

Figure 10:
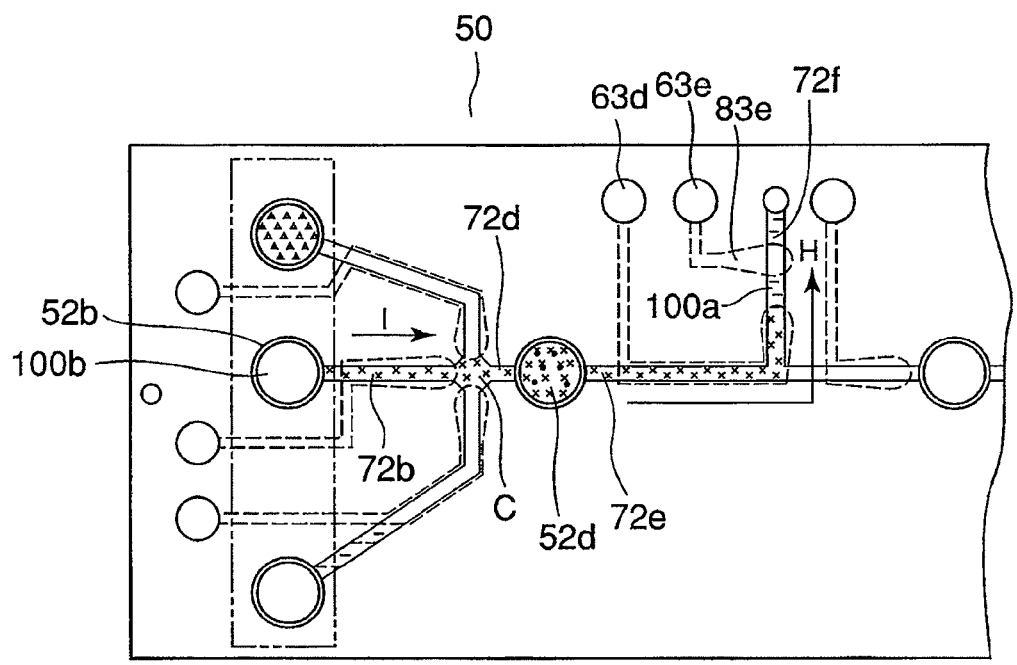
FIG. 10 is a plan view illustrating an operation of the microchip according to the embodiment of this invention.

Next, an operation in a fifth stage is described with reference to FIG. 10. The operation in the fifth stage is a step of delivering the sample 100b packed in the sample reservoir 52b into the reaction reservoir 52d, delivering the sample 100a remaining in the intersecting portion C near the reaction reservoir 52d and the channels 72d and 72e into a vicinity of the disposal hole, and cleaning components other than desired micro components by the sample 100b. From the state of the fourth stage illustrated in FIG. 9, the pressurized medium is applied to the shutter port 63e, and application of the pressurized medium applied to the reaction reservoir 52d and the shutter port 63d is canceled. Then, the pressurized medium is applied from the upper portion of the sample reservoir 52b. As a result, the sample 100b packed in the sample reservoir 52b is guided in an I direction, and is delivered into the reaction reservoir 52d through the channel 72b, the intersecting portion C, and the channel 72d, to thereby be delivered into a halfway point of the channel 72f closed by the channel 72e and the shutter channel 83e. At this time, the sample 100a remaining in a vicinity of the reaction reservoir 52d as illustrated in FIG. 9 is delivered in the H direction into the channel 72f near the shutter channel 83e.

Figure 11:
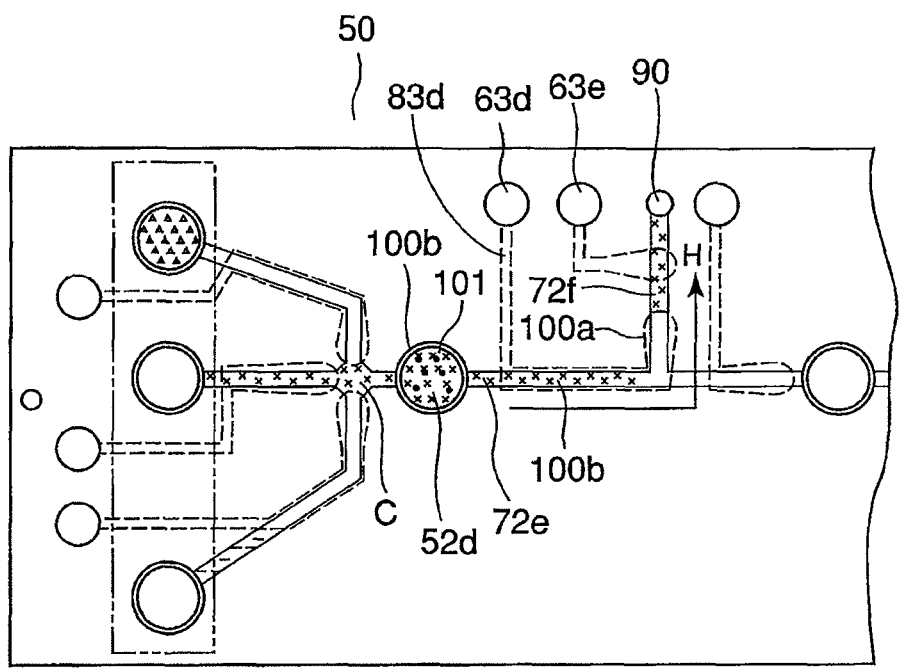
FIG. 11 is a plan view illustrating an operation of the microchip according to the embodiment of this invention.

Next, an operation in a sixth stage is described with reference to FIG. 11. The operation in the sixth stage is a step of disposing of the sample 100a and the sample 100b remaining in the channels 72e and 72f. After canceling application of the pressurized medium applied to the shutter port 63e from the state of the fifth stage illustrated in FIG. 10, the pressurized medium is applied to the shutter port 63d. As a result, the shutter channel 83d is sequentially swelled, and hence the sample 100a and the sample 100b remaining in the channels 72e and 72f are delivered in the H direction to be disposed of through the disposal hole 90. As a result, only the sample 100b remains in vicinities of the reaction reservoir 52d and the intersecting portion C. Further, at this time, the desired micro components are absorbed by the adsorption member 101 in the reaction reservoir 52d, and micro components other than the desired ones are disposed of, that is, cleaned.

Figure 12:
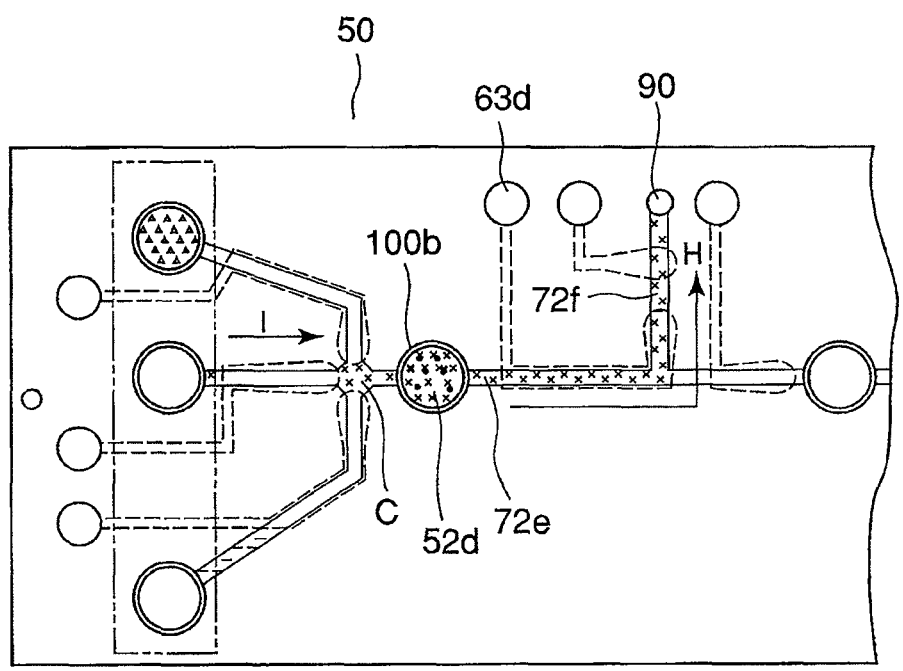
FIG. 12 is a plan view illustrating an operation of the microchip according to the embodiment of this invention.

Next, an operation in a seventh stage is described with reference to FIG. 12. The operation in the seventh stage is a step of disposing of the sample 100b packed in the reaction reservoir 52d in the form of a balloon. After canceling application of the pressurized medium applied to the shutter port 63d from the state of the sixth stage illustrated in FIG. 11, the pressurized medium is pressurized and applied from the upper portion of the reaction reservoir 52d. As a result, the sample 100b packed in the reaction reservoir 52d is delivered in the H direction into the channels 72e and 72f which are exclusively opened, and a part of the sample 100b is disposed of through the disposal hole 90. In other words, the sample 100b in the reaction reservoir 52d is disposed of.

Figure 13:
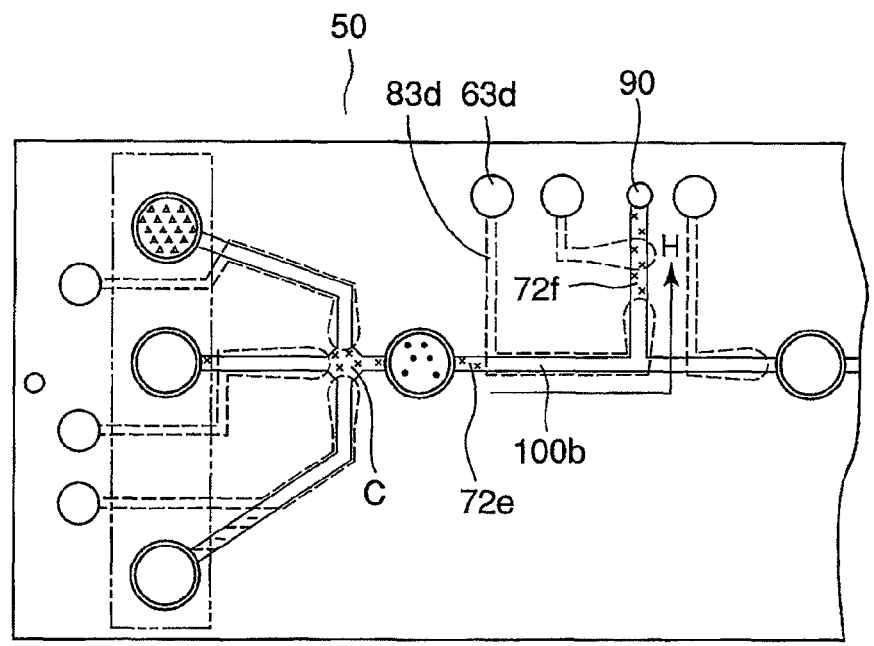
FIG. 13 is a plan view illustrating an operation of the microchip according to the embodiment of this invention.

Next, an operation in an eighth stage is described with reference to FIG. 13. The operation in the eighth stage is a step of disposing of the sample 100*b* remaining in the channels 72*e* and 72*f*. The pressurized medium is applied to the shutter port 63*d* from the state of the seventh stage illustrated in FIG. 12. As a result, the shutter channel 83*d* is sequentially swelled, and hence the sample 100*b* remaining in the channels 72*e* and 72*f* is delivered in the H direction to be disposed of through the disposal hole 90. Further, a part of the sample 100*b* remains in the intersecting portion C.

Figure 14:
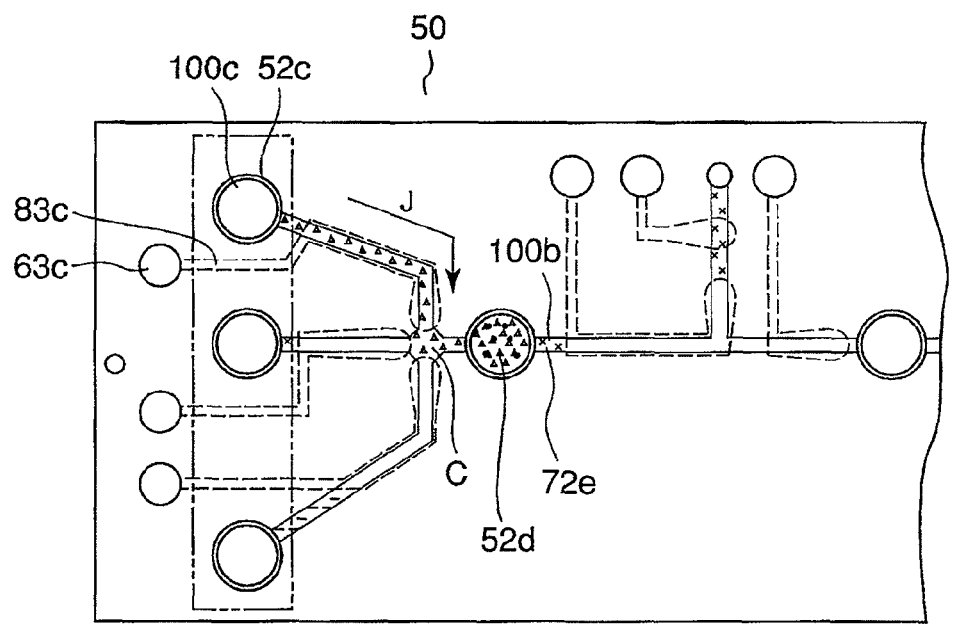
FIG. 14 is a plan view illustrating an operation of the microchip according to the embodiment of this invention.

Next, an operation in a ninth stage is described with reference to FIG. 14. The operation in the ninth stage is a step of delivering the sample 100*c* packed in the sample reservoir 52*c* into the reaction reservoir 52*d*. From the state of the eighth stage illustrated in FIG. 13, application of the pressurized medium applied to the shutter port 63*c* is canceled and the shutter channel 83*c* is opened, and then the pressurized medium is applied to the upper portion of the sample reservoir 52*c*. As a result, the sample 100*c* is delivered in a J direction, and is packed into the inside of the reaction reservoir 52*d* while swelling the reaction reservoir 52*d* into a balloon shape. At this time, a part of the sample 100*b* remaining in the intersecting portion C is squeezed into one end of the channel 72*e* continuous with the reaction reservoir 52*d*.

Figure 15:
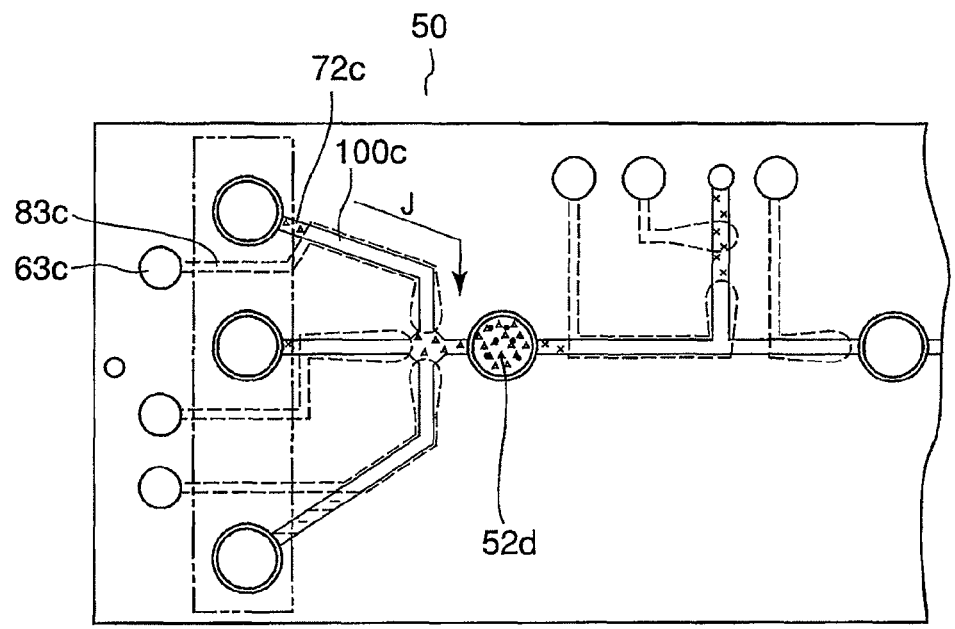
FIG. 15 is a plan view illustrating an operation of the microchip according to the embodiment of this invention.

Next, an operation in a tenth stage is described with reference to FIG. 15. The operation in the tenth stage is a step of squeezing and delivering the sample 100*c* remaining in the channel 72*c* into the reaction reservoir 52*d*. When the pressurized medium is applied to the shutter port 63*c* from the state of the ninth stage illustrated in FIG. 14, the shutter channel 83*c* is swelled, and the sample 100*c* remaining in the portion of the channel 72*c* overlapping the shutter channel 83*c* is squeezed in the J direction. As a result, the sample 100*c* is delivered into the reaction reservoir 52*d*.

Figure 16:
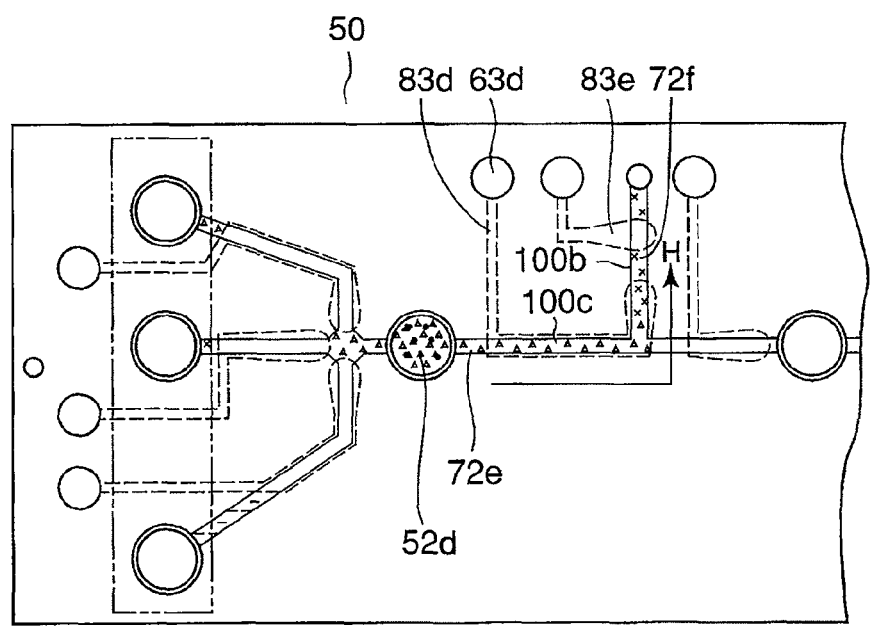
FIG. 16 is a plan view illustrating an operation of the microchip according to the embodiment of this invention.

Next, an operation in an eleventh stage is described with reference to FIG. 16. The operation in the eleventh stage is a step of delivering, into the channel 72*f*, a part of the sample 100*b* delivered into the one end of the channel 72*e* in the tenth stage to remain therein and the sample 100*c*. When canceling application of the pressurized medium applied to the shutter port 63*d* from the state of the tenth stage illustrated in FIG. 15, the shutter channel 83*d* opens the channel 72*e*. At this time, the inside of the reaction reservoir 52*d* is swelled into a balloon shape and has an internal pressure, and hence the inside sample 100*c* is guided in the H direction into the channels 72*e* and 72*f*. At this time, the sample 100*b* remaining in a vicinity of the reaction reservoir 52*d* in the tenth stage is delivered into a vicinity of a portion of the channel 72*f* closed by the shutter channel 83*e*.

Figure 17:
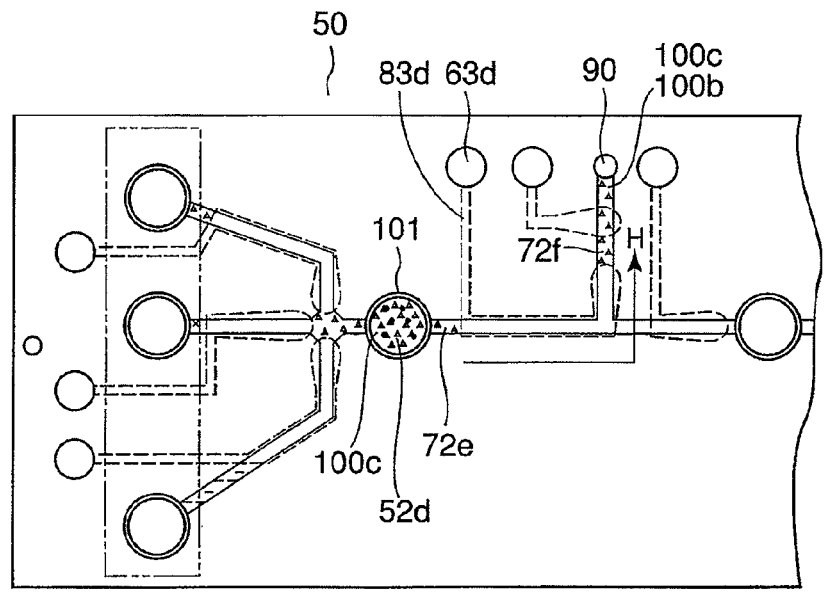
FIG. 17 is a plan view illustrating an operation of the microchip according to the embodiment of this invention.

Next, an operation in a twelfth stage is described with reference to FIG. 17. The operation in the twelfth stage is a step of disposing of the samples 100*b* and 100*c* remaining in the channels 72*e* and 72*f*. When the pressurized medium is applied to the shutter port 63*d* from the state of the eleventh stage illustrated in FIG. 16, the shutter channel 83*d* is swelled, and the sample 100*c* remaining in the channels 72*e* and 72*f* is squeezed in the H direction. As a result, parts of the samples 100*b* and 100*c* remain in the channel 72*f*, and the other parts are disposed of through the disposal hole 90. In other words, in the reaction reservoir 52*d*, only the sample 100*c* is accumulated, and the desired micro components absorbed by the adsorption member 101 are dissolved.

Figure 18:
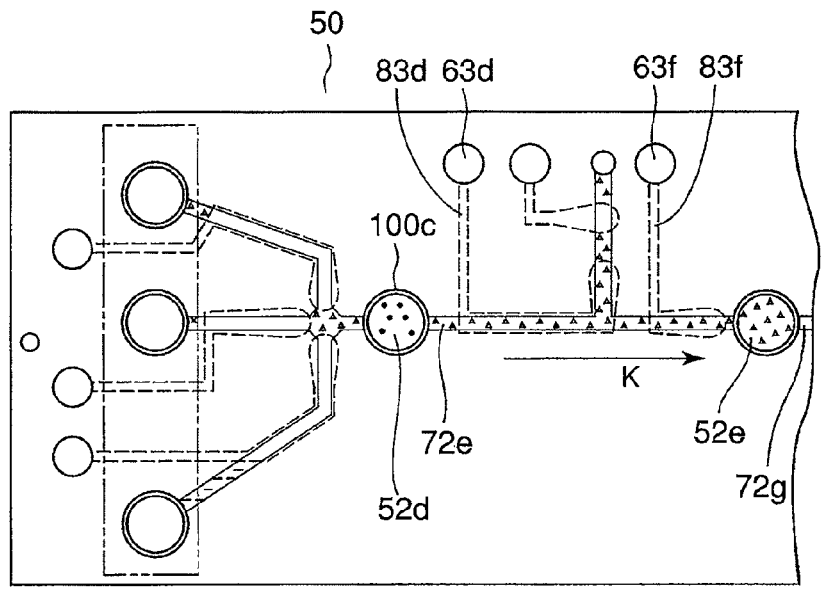
FIG. 18 is a plan view illustrating an operation of the microchip according to the embodiment of this invention.

Next, an operation in a thirteenth stage is described with reference to FIG. 18. The operation in the thirteenth stage is a step of delivering, into the extraction reservoir 52*e*, the sample 100*c* which is accumulated in the reaction reservoir 52*d* and contains the dissolved micro components. Application of the pressurized medium applied to the shutter ports 63*d* and 63*f* is canceled from the state of the twelfth stage illustrated in FIG. 17, and thus the shutter channels 83*d* and 83*f* open the channel 72*e*. Then, the pressurized medium is applied from the upper portion of the reaction reservoir 52*d*. As a result, the sample 100*c* inside the reaction reservoir 52*d* is delivered in a K direction into the channel 72*e* which is exclusively opened. Further, the pressurized medium is applied to the shutter port 63*g* illustrated in FIG. 2, and the shutter channel 83*g* is swelled, to thereby close the channel 72*g*. The sample 100*c* delivered in the K direction swells the extraction reservoir 52*e* into a balloon shape, and is packed in the extraction reservoir 52*e*.

Figure 19:
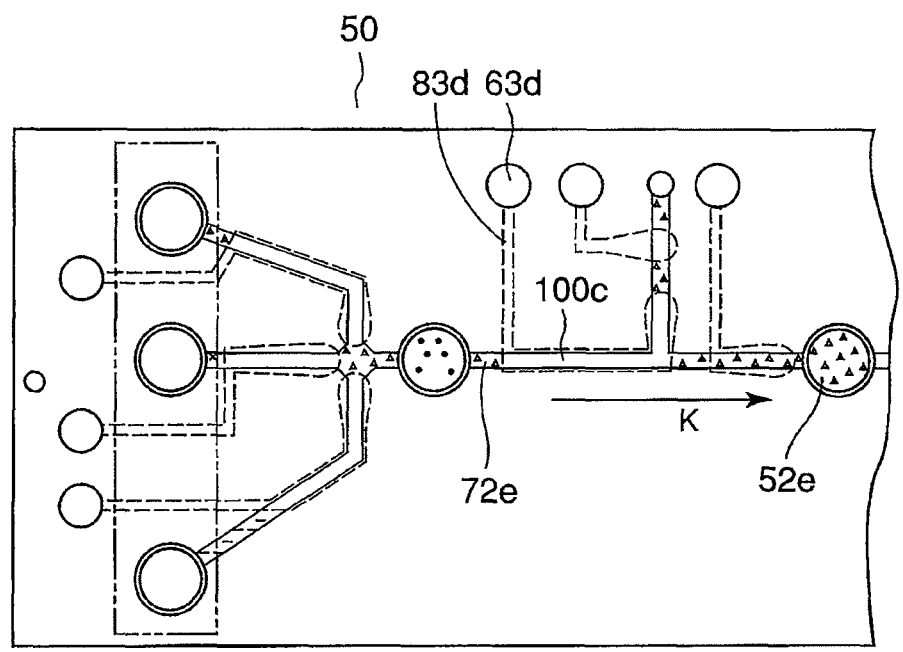
FIG. 19 is a plan view illustrating an operation of the microchip according to the embodiment of this invention.

Next, an operation in a fourteenth stage is described with reference to FIG. 19. The operation in the fourteenth stage is a step of delivering the sample 100*c* remaining in the channel 72*e* into the extraction reservoir 52*e* by the shutter channel 83*d*. When the pressurized medium is applied to the shutter port 63*d* from the state of the thirteenth stage illustrated in FIG. 18, the shutter channel 83*d* is swelled, and the sample 100*c* remaining in the portion of the channel 72*e* overlapping the shutter channel 83*d* is squeezed in the K direction, to thereby be delivered into the extraction reservoir 52*e* through the channel 72*e* which is exclusively opened.

Figure 20:
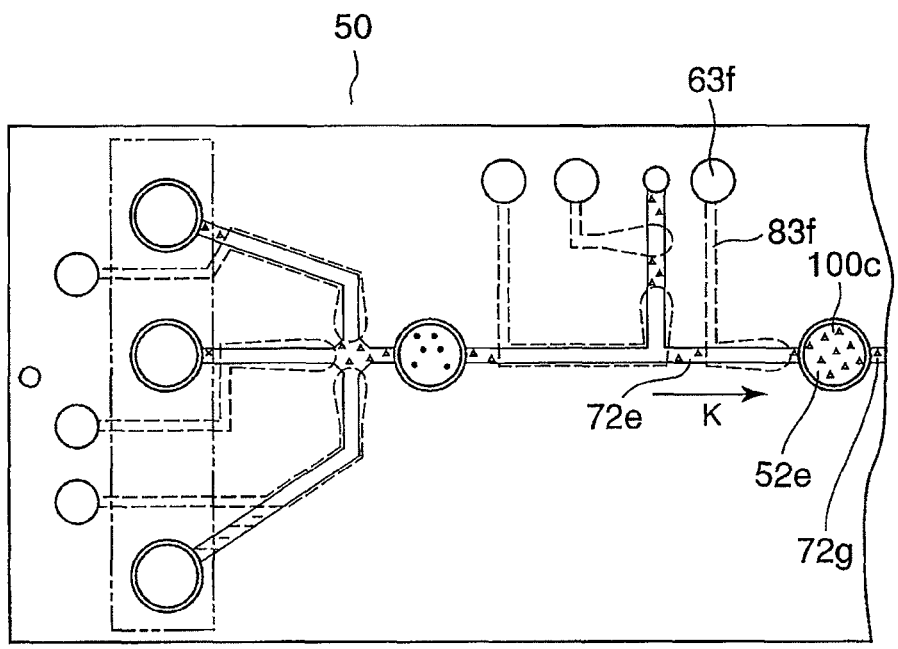
FIG. 20 is a plan view illustrating an operation of the microchip according to the embodiment of this invention.

Next, an operation in a fifteenth stage is described with reference to FIG. 20. The operation in the fifteenth stage is a step of further delivering the sample 100*c* remaining in the channel 72*e* near the extraction reservoir 52*e* into the extraction reservoir 52*e* and of closing the extraction reservoir 52*e*. When the pressurized medium is applied to the shutter port 63*f* from the operation in the fourteenth stage illustrated in FIG. 19, the shutter channel 83*f* is swelled, and hence the sample 100*c* remaining in the channel 72*e* near the extraction reservoir 52*e* is squeezed in the K direction to be delivered into the extraction reservoir 52*e*. Further, the channel 72*g* continuous with the extraction reservoir 52*e* is closed in the previous step, and hence the sample 100*c* packed in the extraction reservoir 52*e* is sealed. In addition, as described in each step, the sample 100*c* which is packed in the extraction reservoir 52*e* and contains the dissolved and desired micro components does not include the samples 100*a* and 100*b* adversely affecting analysis. In other words, the sample 100*c* packed in the extraction reservoir 52*e* allows highly reliable analysis. Further, the sample 100*c* packed in the extraction reservoir 52*e* is further delivered into the second reaction reservoirs 53*a*, 53*b*, and 53*c* through driving a similar structure as illustrated in FIG. 2, and then a subsequent process such as DNA amplification is performed.

In the description of this embodiment, the number of the sample reservoirs is set to three, the number of the reaction reservoir is set to one, the number of the extraction reservoir is set to one, and the number of the second sample reservoirs is set to three. However, the same effect is provided also in the case of adopting a delivering mechanism having the same functions of channels and shutter channels. That is, the number of reservoirs is not limited.

Figure 6:
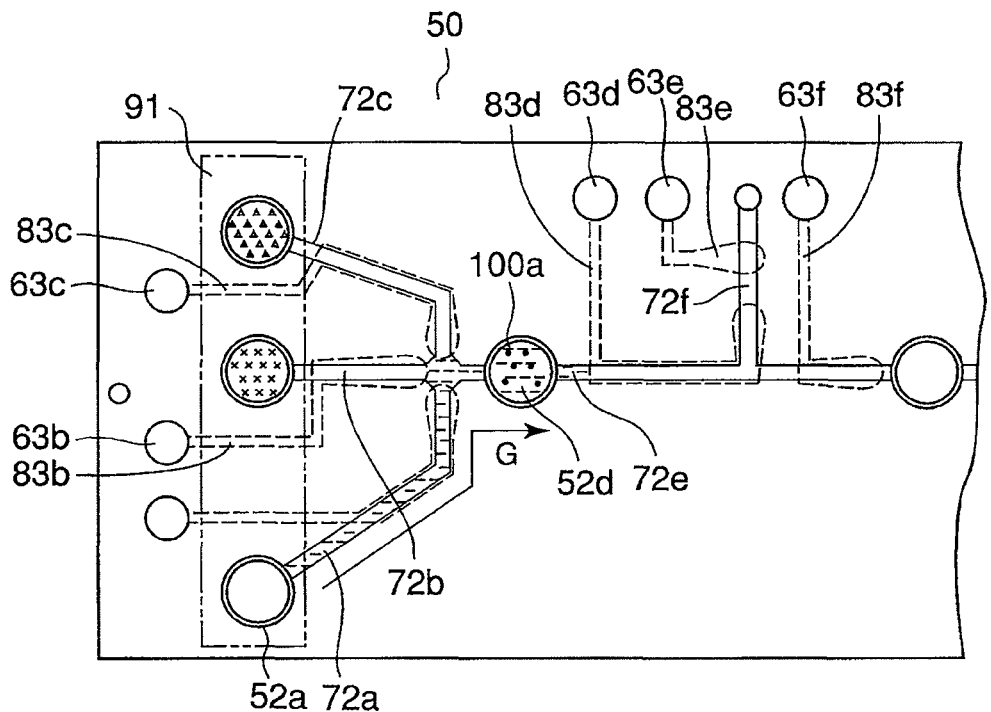
FIG. 6 is a plan view illustrating an operation of the microchip according to the embodiment of this invention.

Further, a circular common region is provided in the intersecting portion C of the channels 72*a*, 72*b*, and 72*c* illustrated in FIG. 6, and parts of leading end portions of the shutter channels 83*a*, 83*b*, and 83*c* are provided to enter the common region. Thus, there is obtained a structure in which the samples are less likely to remain in the intersecting portion C. In other words, a shutter function can be exerted just before the point where the channels intersect. As a result, it is possible to prevent the samples from remaining in a vicinity of the intersecting portion C, and cleaning efficiency of the samples to be delivered is remarkably increased.

Further, the common region C with a circular shape is described in the above-mentioned embodiment. However, the same effect is provided also in the case of adopting the intersecting portion having a common region with an elliptic shape, a rhombic shape, or the like. That is, the shape of the common region is not limited.

Figure 21A:
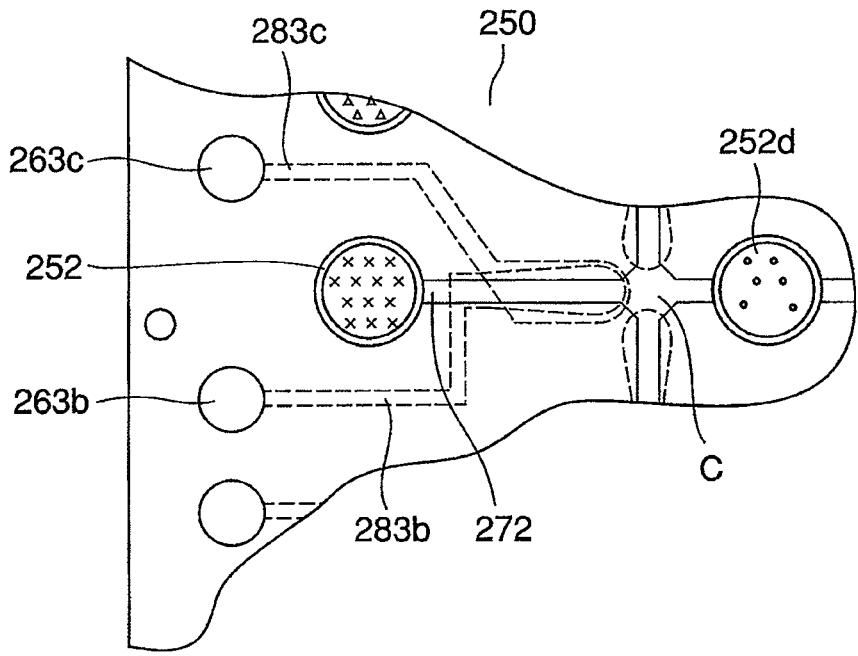
FIGS. 21A and 21B are plan views illustrating an operation of a microchip according to another embodiment of this invention.

Next, another embodiment according to this invention is described with reference to FIG. 21A. FIG. 21A is a plan view illustrating a part of a microchip 250.

Similarly to the above-mentioned embodiment, a sample reservoir 252 and a reaction reservoir 252d are provided on the microchip 250, and a channel 272 is continuous with the reaction reservoir 252d through the intersecting portion C in which the channel 272 intersects another channels. Similarly to the above-mentioned embodiment, a channel 283b is continuous with a shutter port 263b while being provided to a layer different from a layer provided with the channel 272, and one end of the channel 283b is provided while partially overlapping the channel 272 in a length direction and extending below the channel 272 and is guided to the inside of the intersecting portion C. Moreover, a channel 283c is continuous with a shutter port 263c while being provided to a layer different from the layer provided with the channel 272 and the layer provided with the channel 283b, and one end of the channel 283c is provided while partially overlapping the channel 272 in the length direction and extending below the channel 272 and is guided to the inside of the intersecting portion C. The channel 283c and the channel 283b press the channel 272 forward, and hence it is possible to close the channel 272, and to squeeze the sample remaining in the channel 272.

Figure 21B:
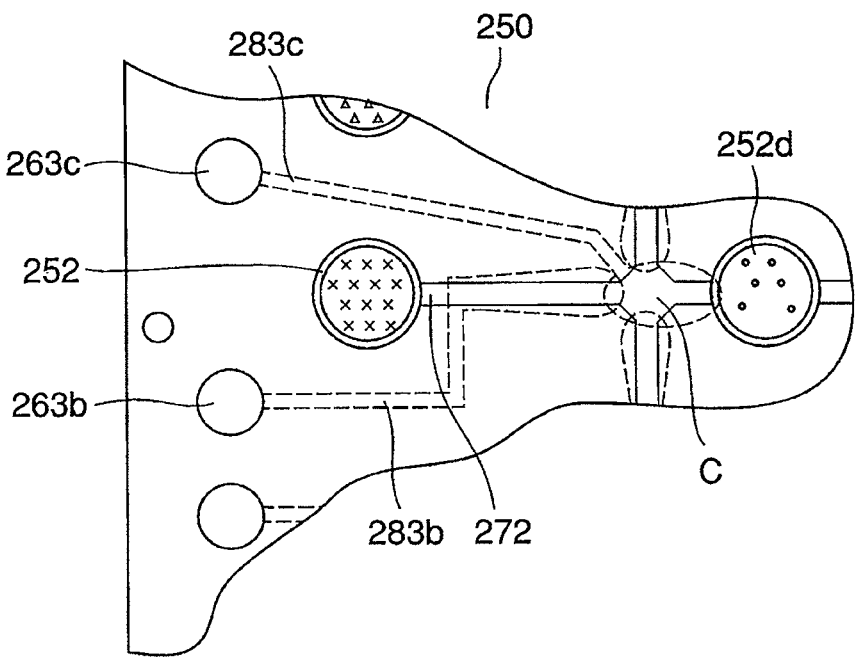

Next, another embodiment according to this invention is described with reference to FIG. 21B. FIG. 21B is a plan view illustrating a part of the microchip 250.

Similarly to the above-mentioned embodiment, the sample reservoir 252 and the reaction reservoir 252d are provided on the microchip 250, and the channel 272 is continuous with the reaction reservoir 252d through the intersecting portion C in which the channel 272 intersects another channels. Further, unlike the above-mentioned embodiment, the channel 283c is continuous with the shutter port 263c while being provided to a layer different from the layer provided with the channel 272, and one end of the channel 283c is provided while overlapping the channel between the intersecting portion C and the reaction reservoir 252d. Through pressing the channel 283c forward, it is possible to close the channel between the intersecting portion C of the channel 272 and the reaction reservoir 252d, and to squeeze the sample remaining in the channel 272. Further, through increasing the number of channels continuous with the shutter port owing to an increase of layers for channels continuous with the shutter port, etc., it is possible to squeeze all of the sample remaining in the channel through which the sample passes.

Further, the shutter port 263c is provided in the microchip 250, and the channel 283c is continuous with the shutter port 263c. In addition, the shutter channel 283c is provided to an upper layer different from the layer provided with the channel 272, and one end of the channel 283c is provided while partially overlapping the channel 272 in the length direction and extending above the channel 272 and is guided to the inside of the intersecting portion C. In other words, unlike the above-mentioned embodiment, the channel 272 is sandwiched between the shutter channels 283b and 283c.

With the above-mentioned structure, when the pressurized medium is applied to the shutter ports 263b and 263c simultaneously, the shutter channels 283b and 283c compress the channel 272 from the upper layer and the lower layer. Thus, in comparison with the structure illustrated in FIG. 5, a function of closing the channels and a function of squeezing are remarkably improved. That is, in the microchip having a laminated structure formed of elastic members, it is not always necessary that one shutter channel corresponds to one channel serving as an object to be controlled. Also in the case where a plurality of shutter channels correspond to one channel, the same or higher function is obtained.

Figure 22A:
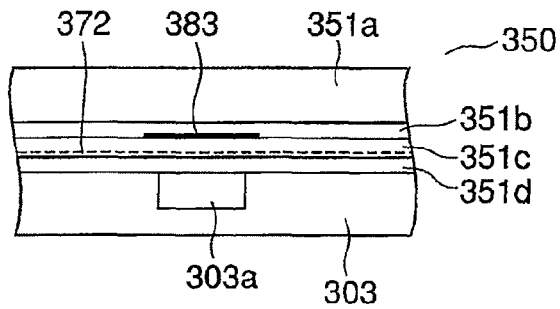
FIGS. 22A and 22B are plan views illustrating an operation of a microchip according to another embodiment of this invention.
Figure 22B:
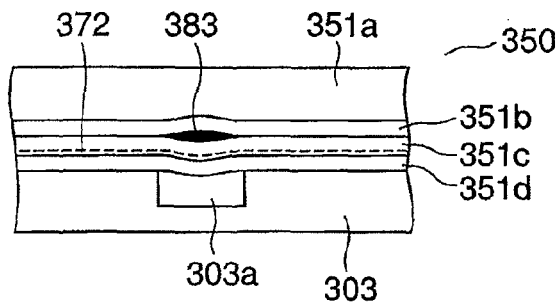

Next, another embodiment according to this invention is described with reference to FIG. 22. FIGS. 22A and 22B are sectional views of a microchip 350.

The microchip 350 has a laminated structure including a main plate 351a, a second plate 351b, a third plate 351c, and a fourth plate 351d which are each formed of an elastic member. A channel 372 has a micro linear shape, and is constituted by a channel portion in a non-bonded state between the third plate 351c and the fourth plate 351d. Further, a shutter channel 383 has a micro linear shape, and is constituted by a channel portion in a non-bonded state between the second plate 351b and the third plate 351c. For convenience of description, FIG. 22 illustrate the channels as if each of the channels has a volume. However, the actual volume is next to zero. Further, in a table 303 on which the microchip 350 is mounted, a dented portion 303a with a recessed shape is provided at a position corresponding to an intersecting portion of the channel 372 and the shutter channel 383.

Next, an operation of the dented portion 303a is described with reference to FIG. 22B. Under the device structure illustrated in FIG. 22A, when the pressurized medium is applied to the shutter channel 383, the shutter channel 383 deforms the main plate 351a, the second plate 351b, the third plate 351c, and the fourth plate 351d which are each formed of the elastic member. At this time, the third plate 351c and the fourth plate 351d are deformed downward together with the channel 372 formed between the third plate 351c and the fourth plate 351d, and are swelled in a protruding manner toward the inside of the dented portion 303a. As a result, the channel 372 is brought into press-contact with a periphery of the dented portion 303a, and is closed firmly. That is, with provision of the dented portion in the table 303, a function of closing the channel is improved.

The case of providing the dented portion 303a is described with reference to FIGS. 22A and 22B. However, the same effect is provided also in the case of providing a hole portion in the microchip or laminating a separate microchip provided with a hole portion. That is, no limitation is imposed on the shape.

Figure 23:
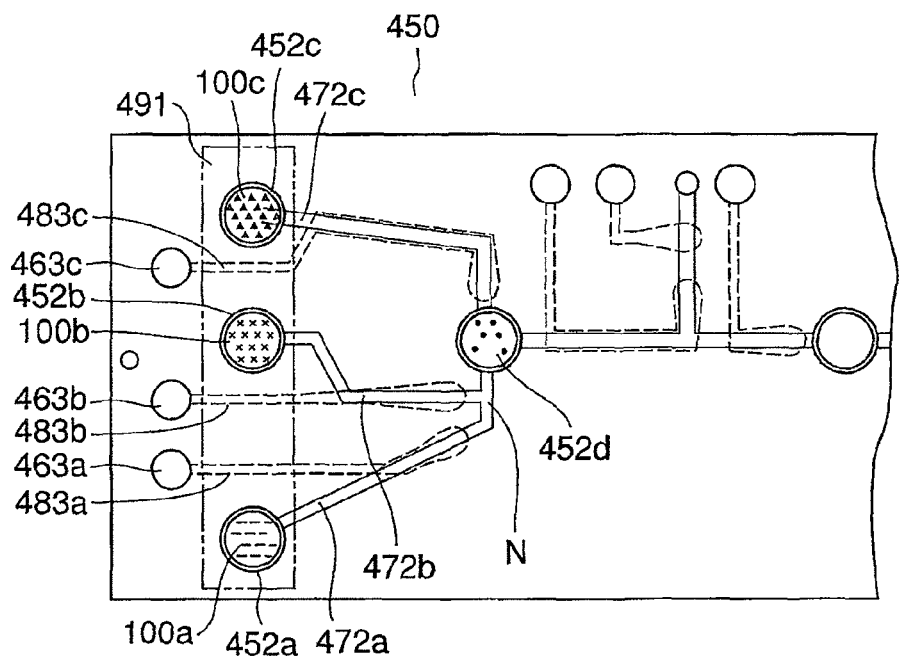
FIG. 23 is a plan view illustrating an operation of a microchip according to another embodiment of this invention.

Next, another embodiment according to this invention is described with reference to FIG. 23. FIG. 23 is a plan view illustrating a part of a microchip 450.

In the same manner as that illustrated in FIG. 3(a), sample reservoirs 452a, 452b, and 452c on the microchip 450 are packed with the samples 100a, 100b, and 100c, respectively, and upper portions of the sample reservoirs are covered with a film 491. Further, in the same manner as that illustrated in FIG. 4, a reaction reservoir 452d is in the form of a balloon. Moreover, channels 472a and 472b are continuous with the sample reservoirs 452a and 452b, respectively, and one end of each of the channels 472a and 472b is continuous with the reaction reservoir 452d through an intersecting portion N. Further, one end of a channel 472c is continuous with the sample reservoir 452c, and the other end thereof is continuous directly with the reaction reservoir 452d.

In addition, shutter ports 463a, 463b, and 463c having the same structures as those of the shutter ports 63a, 63b, and 63c illustrated in FIGS. 2 and 5 are provided in the microchip 450. Shutter channels 483a, 483b, and 483c are continuous with the shutter ports 463a, 463b, and 463c, respectively. In the same manner as that illustrated in FIG. 2, one end of each of the shutter channels 483a, 483b, and 483c is provided while extending below the channels 472a, 472b, and 472c, respectively.

With the above-mentioned structure, similarly to the microchip 50 illustrated in FIG. 5, the samples 100a, 100b, and 100c packed in the sample reservoirs 452a, 452b, and 452c are sequentially delivered into the reaction reservoir 452d in the same manner as that illustrated in FIG. 5. In this case, the channel 472c and a channel group including the channels 472a and 472b are independently continuous with the reaction reservoir 452d, and hence the sample 100a adversely affecting analysis of the sample 100c does not contaminate the channel 472c for the sample 100c. Moreover, for the sample 100c to be injected into the reaction reservoir 452d, the inside of the reaction reservoir 452d is cleaned by the sample 100b which is delivered after the sample 100a and has a cleaning function. In other words, the sample 100c and the sample 100a are not mixed with each other before being introduced into the reaction reservoir 452d, and thus no mutual contamination occurs. In addition, at least one of the sample reservoirs 452a, 452b, and 452c is packed with a sample for stabilizing the channels at an initial stage, and the sample is delivered at the initial stage or a desired step to separate the non-bonded portions of the channels of the microchip, to thereby enable to achieve stabilization.

Further, at least one of the sample reservoirs 452a, 452b, and 452c is packed with a sample which stabilizes the channels and does not adversely affect another samples, and the sample is delivered at the initial stage or the desired step to be packed into the points just before the sample reservoirs and the reaction reservoir of the microchip and narrow portions between the channels owing to capillary phenomenon. In this way, the samples to be used in respective steps are prevented from entering the narrow portions of the microchip, and hence it is possible to prevent mixture of the samples before introduction into the reaction reservoir 452d, and to eliminate the mutual contamination.

As a result, mixture of the samples causing the mutual contamination is prevented, and accuracy in analyzing the micro components is increased. In each of the above-mentioned embodiments, the case where the number of the sample reservoirs is three is described. However, channels for samples, in which the mutual contamination occurs, are independently provided, and thus the same effect is provided also in the case where the number of the sample reservoirs is plural. That is, the number of the sample reservoirs is not limited.

As described above, in the channel control mechanism for a microchip according to each of the embodiments of this invention, a channel opening/closing mechanism has the following structure. Specifically, the channel opening/closing mechanism partially intersects a sample channel which is formed in the microchip to be sealed by the elastic members, and a pressurizing channel is provided to a layer different from a layer provided with the channel. When the pressurized medium is applied to the pressurizing channel, the pressurizing channel is brought into press-contact with the channel at the intersecting portion, to thereby close the channel.

Under this structure, the pressurizing channel serves as a closing mechanism for pressing the channel from the layer near the channel formed and sealed in the elastic members. Thus, it is possible to reliably block the channel.

Further, the delivering channels, which are continuous with the reaction reservoir as a delivered side and through which samples are sequentially and concentratedly delivered from a plurality of sample reservoirs as a delivering side, are constituted by channels independent for each sample group which adversely affects analysis when being mixed with another sample group. The delivering channels have a channel structure of preventing, during sequent deliver, contamination caused by the sample remaining in the channel and bringing adverse effect and of avoiding the adverse effect on analysis.

Under this structure, through separating the inflow channels through which the samples adversely affecting each other are delivered into the reaction reservoir, the samples are not delivered through overlapping channels, and hence reliability of analysis is increased.

Further, as a mechanism for squeezing the sample remaining in the channel, the following mechanism is adopted. Specifically, in the mechanism, the pressurizing channel and the channel, which are provided to different layers, overlap each other at an overlapping portion in a length direction of the channel through a film of the elastic member. When the pressurized medium is applied to the pressurizing channel, the pressurizing channel closes the channel, and sequentially squeezes the sample remaining in the channel along with forward swelling of the overlapping portion.

Under this structure, the channel and the pressurizing channel formed and sealed in the elastic members overlap each other at the overlapping portion in the length direction of the channel, and exert the function of squeezing the sample in the channel. As a result, the sample remaining in the channel is delivered into the delivered side and the sample reservoirs as the delivering side, and hence the sample does not remain in the channel. Thus, it is possible to prevent contamination caused by the sample to be delivered through the same channel in a next step, to thereby increase reliability of analysis. In addition, the sample remaining in the channel can be used after being squeezed, and hence it is possible to save an expensive sample, that is, to reduce analysis cost.

Further, at the intersecting portion of the plurality of channels, one end of the pressurizing channel for closing/opening each of the channels is protruded in the intersecting portion. Thus, when another channel is opened in the intersecting portion and the sample is delivered therein, the sample is prevented from contaminating the inside of the channel closed by the pressurizing channel, and the sample is prevented from remaining in the intersecting portion.

Under this structure, at the position where the plurality of channels intersect, the pressurizing channel for closing each of the channels overlaps a part of the intersecting portion to be protruded in the intersecting portion, and thus the sample, which is being delivered into the channel other than the channel closed in the intersecting portion, does not flow into a vicinity of the intersecting portion of the closed channel. Therefore, the channel is reliably cleaned when a cleaning sample is delivered into the intersecting portion, contamination caused by mixture of the samples is avoided, and reliability of analysis is increased.

Further, the channel opening/closing mechanism has the following structure. Specifically, the channel opening/closing mechanism partially intersects the sample channel which is formed in the microchip to be sealed by the elastic members. Moreover, the pressurizing channel is provided to a layer different from the layer in which the channel is formed, and a hole portion or a recessed portion is provided in the microchip or a member for sandwiching the microchip at a position corresponding to the intersecting portion of the channel. When the pressurized medium is applied to the pressurizing channel, the channel formed of the elastic members is deformed at the intersecting portion, and is deformed to enter the hole portion or the recessed portion, to thereby sandwich and close the channel at an edge portion of the hole portion or the recessed portion.

Under this structure, in the structure in which the pressurized medium is applied to the pressurizing channel and thus the elastic members are deformed to close the channel in a press-contact state, the channel is deformed to enter the hole portion or the recessed portion, to thereby increase the closing function. As a result, the pressure of the pressurized medium is reduced, and energy saving is achieved. In addition, another samples are prevented from entering, and hence reliability of analysis is increased.

Further, for a method of injecting the sample, the following structure is adopted. Specifically, at least one of the plurality of sample reservoirs as the delivering side is packed with a sample or a cleaning sample for preparing the states of the sample reservoirs as the delivering side and the states of the channels, and the sample is delivered at the beginning of the delivering step or during the desired step.

Under this structure, the cleaning or channel-stabilizing sample packed in the at least one of the sample reservoirs is delivered into the channel in the microchip at an initial stage of analysis or at the necessary time. Thus, the delivering mechanism changes the sample remaining in the channel into the sample not adversely affecting analysis in the post-steps, removes the sample remaining and bringing adverse effect, and stabilizes the state of the channel, to thereby increase reliability of analysis.

As described above, according to the channel control mechanism for a microchip according to each of the embodiments of this invention, it is possible to squeeze and analyze the sample remaining in the channel, and hence an expensive sample is saved.

Further, according to the channel opening/closing mechanism for a microchip as described above, it is possible to reliably close the channels involved in delivering the samples, and thus the samples are not mixed with each other. As a result, it is possible to avoid deterioration of analyzing accuracy caused by the mutual contamination, and to remarkably increase reliability of analysis.

Still further, according to the channel opening/closing mechanism for a microchip as described above, it is possible to achieve simple control, a reduction in size and weight of the device, energy saving, and provision of an inexpensive device.

Figure 24:
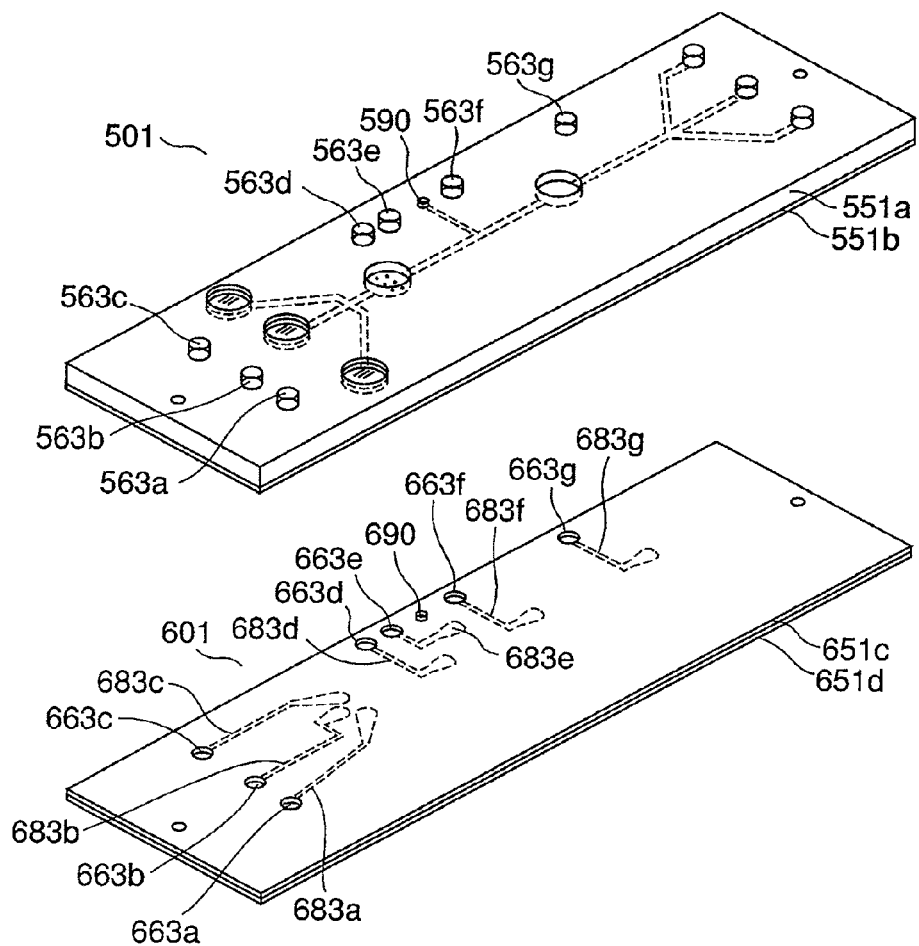
FIG. 24 is a perspective view illustrating a structure of a microchip according to another embodiment of this invention.

Next, another embodiment of this invention is described with reference to FIG. 24. FIG. 24 illustrates a structure in which the microchip 50 illustrated in FIG. 2 is separated into a chip body 501 and a shutter unit 601.

The chip body 501 has a multi-layer structure, and has a laminated structure formed of a main plate 551a and a second plate 551b which is made of a stretchable resin. The chip body 501 includes shutter ports 563a, 563b, 563c, 563d, 563e, 563f, and 563g passing through the main plate 551a and the second plate 551b. In addition, the chip body 501 includes a chip disposal hole 590 passing through the second plate 551b downward. Another structure is the same as that of the microchip 50 illustrated in FIG. 2.

Meanwhile, the shutter unit 601 has a laminated structure formed of a first shutter plate 651c made of a stretchable resin and a second shutter plate 651d. In addition, the shutter unit 601 includes shutter ports 663a, 663b, 663c, 663d, 663e, 663f, and 663g passing through the first shutter plate 651c. Further, shutter channels 683a, 683b, 683c, 683d, 683e, 683f, and 683g each having an opened end are connected with the shutter ports 663a, 663b, 663c, 663d, 663e, 663f, and 663g, respectively. Further, a chip disposal hole 690 is formed to pass through the first shutter plate 651c and the second shutter plate 651d. When the chip body 501 and the shutter unit 601 are superimposed on each other, the shutter ports 563a, 563b, 563c, 563d, 563e, 563f, and 563g correspond in position to the shutter ports 663a, 663b, 663c, 663d, 663e, 663f, and 663g, respectively, and the chip disposal hole 590 corresponds in position to the chip disposal hole 690.

The shutter channels 683a, 683b, 683c, 683d, 683e, 683f, and 683g are provided between the first shutter plate 651c and the second shutter plate 651d, and are formed of non-bonded portions. Further, when the pressurized medium is applied from each of the shutter ports 663a, 663b, 663c, 663d, 663e, 663f, and 663g, the medium flows into each of the shutter channels to swell each of the shutter channels into a balloon shape between the first shutter plate 651c and the second shutter plate 651d.

With the above-mentioned structure, when, after being superimposed on each other, the chip body 501 and the shutter unit 601 are mounted onto the device illustrated in FIG. 1 and are sandwiched between the table 3 and the cover 20, the chip body 501 and the shutter unit 601 exert the same function as that of the microchip 50 illustrated in FIG. 2. In other words, it is possible to separately place the shutter portion of the microchip 50 as in the case of the shutter unit 601, and thus a structure of a chip main body is simplified.

Figure 25:
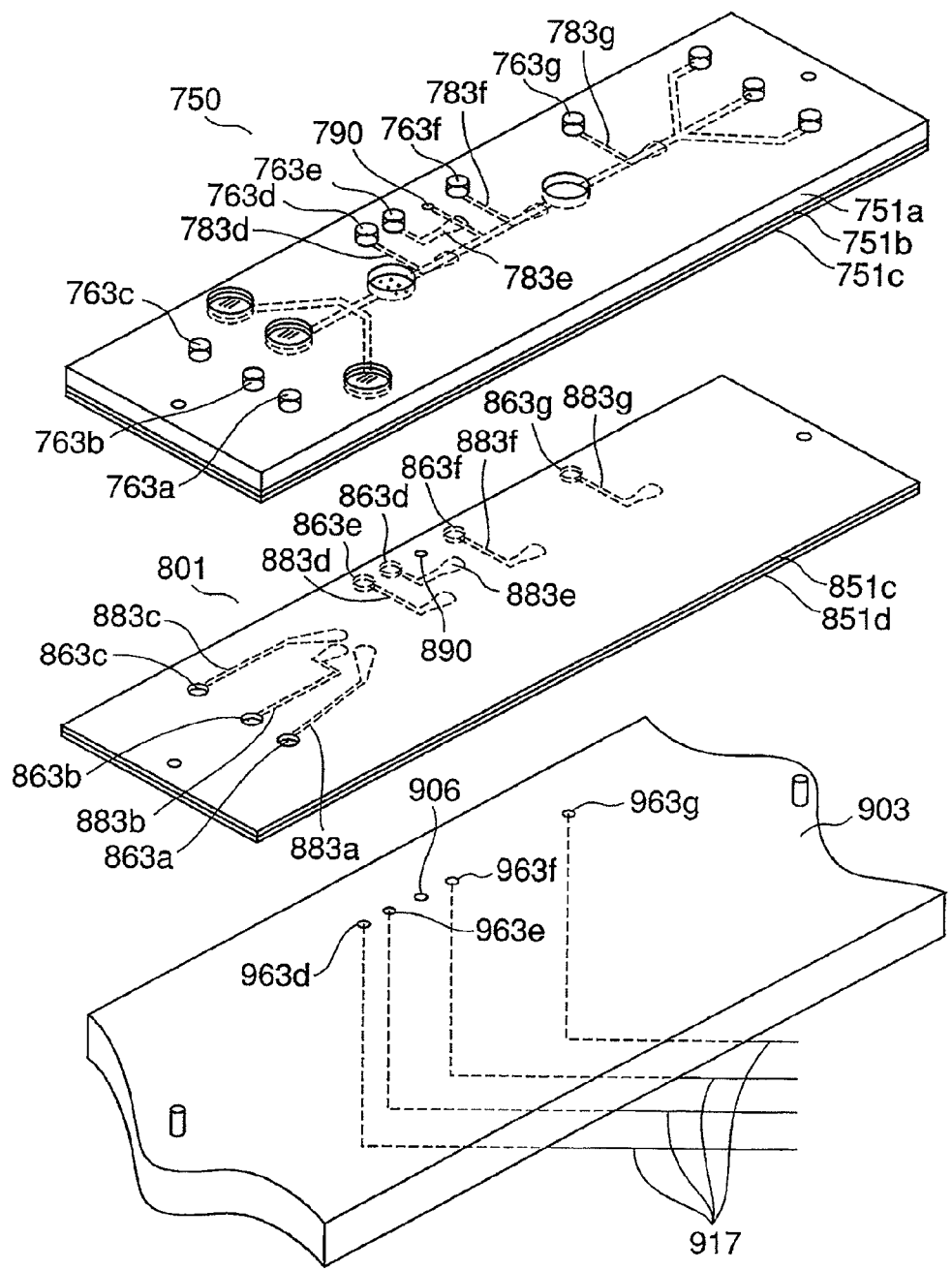
FIG. 25 is a perspective view illustrating a structure of a microchip according to another embodiment of this invention.

In addition, another embodiment of this invention is described with reference to FIG. 25. FIG. 25 illustrates a structure in which the microchip 50 illustrated in FIG. 2 is separated into a chip body 750 and a shutter unit 801.

The chip body 750 has a multi-layer structure, and has a laminated structure formed of a main plate 751a and a second plate 751b and a third plate 751c which are made of a stretchable resin. The chip body 750 includes shutter ports 763a, 763b, and 763c passing through the main plate 751a, the second plate 751b, and the third plate 751c. In addition, the chip body 750 includes a chip disposal hole 790 passing through the second plate 751b and the third plate 751c downward.

In addition, the chip body 750 includes shutter ports 763d, 763e, 763f, and 763g passing through the main plate 751a and the second plate 751b. Further, shutter channels 783d, 783e, 783f, and 783g formed of non-bonded portions are provided between the main plate 751a and the second plate 751b, and one end of each of the shutter channels is continuous with/opened to each of the shutter ports 763d, 763e, 763f, and 763g.

Further, the channels 72a, 72b, 72c, 73d, 73d, 73e, 73f, and 73g illustrated in FIG. 2 are provided in a non-bonded state between the second plate 751b and the third plate 751c illustrated in FIG. 25. In other words, the shutter channels 783d, 783e, 783f, and 783g intersect the channels 72a, 72b, 72c, 73d, 73d, 73e, 73f, and 73g through the second plate 751b.

In addition, the shutter unit 801 has a laminated structure formed of a first shutter plate 851c and a second shutter plate 851d formed of elastic members, and shutter channels 883a, 883b, 883c, 883d, 883e, 883f, and 883g are provided in a partially non-bonded state between the first shutter plate 851c and the second shutter plate 851d. Further, shutter ports 863a, 863b, and 863c passing through the first shutter plate 851c and shutter ports 863d, 863e, 863f, and 863g passing through the second shutter plate 851d downward are provided. In addition, one end of each of the shutter channels 883a, 883b, 883c, 883d, 883e, 883f, and 883g is continuous with/opened to each of the shutter ports 863a, 863b, 863c, 863d, 863e, 863f, and 863g. In other words, when the pressurized medium is applied to each of the shutter ports 863a, 863b, 863c, 863d, 863e, 863f, and 863g, each of the shutter channels 883a, 883b, 883c, 883d, 883e, 883f, and 883g is swelled into a balloon shape to be brought into press-contact with the chip body 750 from below. Further, the shutter unit 801 includes a disposal hole 890 passing through the first shutter plate 851c and the second shutter plate 851d.

Further, in a table 903 on which the chip body 750 and the shutter unit 801 are mounted in a superimposed state, shutter pressurizing ports 963d, 963e, 963f, and 963g are provided to pass through the table 903, and are connected with tubes 917, respectively. The tubes 917 are respectively connected with the same solenoid-controlled valves as the shutter solenoid-controlled valves 18a to 18g illustrated in FIG. 1, and are controlled in application of the pressurized medium. In addition, a disposal hole 906 is provided in the table 903, and is connected with the disposal reservoir 8 through the disposal solenoid-controlled valve 7 similarly to the disposal hole 6 illustrated in FIG. 1.

In addition, when, after being superimposed on each other, the chip body 750 and the shutter unit 801 are mounted onto the table 903 and are sandwiched by the cover 20 illustrated in FIG. 1, the chip body 750 and the shutter unit 801 are mounted in a superimposed state so that the shutter ports 763a, 763b, and 763c respectively correspond in position to the shutter ports 863a, 863b, and 863c and the shutter ports 863d, 863e, 863f, and 863g respectively correspond in position to the shutter ports 963d, 963e, 963f, and 963g and the chip disposal hole 790, the disposal hole 890, and the disposal hole 906 correspond in position to each other.

In other words, the pressurized medium applied to each of the shutter ports 763d, 763e, 763f, and 763g swells each of the shutter channels 783d, 783e, 783f, and 783g into a balloon shape in the chip body 750, to thereby close the channel. Further, the pressurized medium applied to each of the shutter ports 763a, 763b, and 763c swells each of the shutter channels 883a, 883b, and 883c in the shutter unit 801 into a balloon shape through each of the shutter ports 863a, 863b, and 863c, to thereby close the channel in the chip body 750 from a downward direction. Further, the pressurized medium applied to each of the shutter ports 963d, 963e, 963f, and 963g swells each of the shutter channels 883d, 883e, 883f, and 883g in the shutter unit 801 into a balloon shape through each of the shutter ports 863d, 863e, 863f, and 863g, to thereby close the channel in the chip body 750 from a downward direction.

As a result, the shutter channels 763d, 763e, 763f, and 763g and the shutter channels 883d, 883e, 883f, and 883g close the channels in the chip body 750 from upward and downward directions, and thus a firm closing mechanism is obtained. With provision of the above-mentioned structure, blocking means equal to or firmer than the microchip 50 illustrated in FIG. 2 is obtained.

Figure 26:
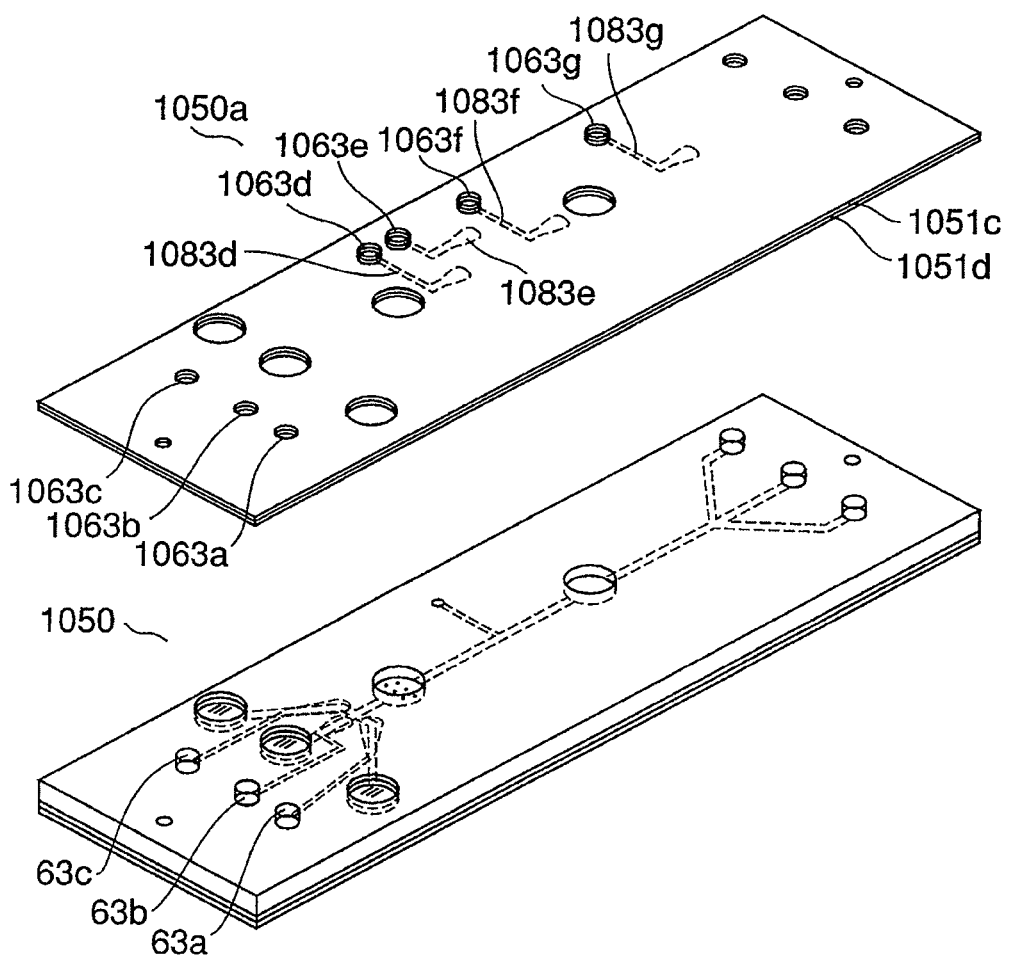
FIG. 26 is a perspective view illustrating a structure of a microchip according to another embodiment of this invention.

In addition, another embodiment of this invention is described with reference to FIG. 26. A chip body 1050 has a structure similar to the structure of the microchip 50 illustrated in FIG. 2. However, the chip body 1050 does not include the shutter ports 63d, 63e, 63f, and 63g and the shutter channels 83d, 83e, 83f, and 83g.

Further, a shutter unit 1050 has a laminated structure formed of a first shutter plate 1051c formed of a stretchable member and a second shutter plate 1051d, and shutter channels 1083d, 1083e, 1083f, and 1083g are provided in a partially non-bonded state between the first shutter plate 1051c and the second shutter plate 1051d.

Still further, shutter ports 1063d, 1063e, 1063f, and 1063g passing through the first shutter plate 1051c are provided. In addition, one end of each of the shutter channels 1083d, 1083e, 1083f, and 1083g is continuous with/opened to each of the shutter ports 1063d, 1063e, 1063f, and 1063g. In other words, when the pressurized medium is applied to each of the shutter ports 1063d, 1063e, 1063f, and 1063g, each of the shutter channels 1083d, 1083e, 1083f, and 1083g is swelled into a balloon shape to be brought into press-contact with the chip body 1050 from above.

Further, in the shutter unit 1050a, shutter ports 1063a, 1063b, and 1063c passing through the first shutter plate 1051c and the second shutter plate 1051d are provided at positions corresponding to the shutter ports 63a, 63b, and 63c of the chip body 1050 when the shutter unit 1050a is superimposed on the chip body 1050. In addition, there are provided through-holes through which an operation of the chip body 1050a is performed.

Next, after being superimposed on each other, the chip body 1050 and the shutter unit 1050a are mounted onto the device illustrated in FIG. 1 and are sandwiched between the cover 20 and the table 3, and the previously-set program is executed. Accordingly, the pressurized medium is applied to each of the shutter ports 1063d, 1063e, 1063f, and 1063g, and each of the shutter channels 1083d, 1083e, 1083f, and 1083g is swelled. As a result, each of the shutter channels 1083d, 1083e, 1083f, and 1083g is brought into press-contact with each of the channels 72e, 72f, and 72g illustrated in FIG. 2, to thereby close the same. As seen in the above description, the same effect is provided also in the case of placing the shutter unit 1050a above the chip body 1050.

That is, as described above, the same effect is provided in the case of placing the shutter unit above or below the chip body, or even in the case of placing the shutter units above and below the chip body, and no limitation is imposed on where to place.

Hereinabove, this invention which has been made by the inventor of this invention is described in detail based on the embodiments. However, it is needless to say that this invention is not limited to the above-mentioned embodiments, and various modifications can be made without departing from the gist of this invention.

This invention is based on Japanese Unexamined Patent Application Publication (JP-A) No. 2008-075395 filed on Mar. 24, 2008, and hence contents disclosed in the above-mentioned patent application are all incorporated in this application.

The invention claimed is:

1. A microchip comprising:
a first layer;
a second layer;
an intermediate layer which is provided between the first layer and the second layer and which comprises an elastic member;
a sample-delivering reservoir which packs a sample therein;
a sample-delivered reservoir to which the sample is delivered;
a channel which is provided between the first layer and the intermediate layer and which connects the sample-delivering reservoir and the sample-delivered reservoir; and
a first shutter portion which is provided between the second layer and the intermediate layer and which overlaps the channel from a predetermined position of the channel to a vicinity of the sample-delivered reservoir;
wherein the microchip is configured so that the channel is closed by applying pressure to the first shutter portion while the channel is opened by releasing the pressure to the first shutter portion.

2. A microchip according to claim 1, wherein:
the first shutter portion at least partially overlaps the channel in a length direction of the channel, and
the microchip is configured so that, by applying pressure to the first shutter portion, at least a part of the sample remaining in the channel overlapping the first shutter portion flows to the sample-delivered reservoir.

3. A microchip according to claim 1, further comprising:
a third layer which is provided opposite to the intermediate layer with respect to the first layer; and
a second shutter portion which is provided between the first layer and the third layer and which overlaps the channel;
wherein the channel is sandwiched by the first and the second shutter portions.

4. A microchip according to claim 1, wherein a hole portion is provided in a portion corresponding to a position at which the channel and the first or a second shutter portion overlap each other.

5. A microchip according to claim 4, wherein the microchip is configured to close the channel in a manner such that, when applying pressure to the first or the second shutter portion to bring the first or the second shutter portion into pressing contact with the channel, the channel is deformed through the intermediate layer to enter the hole portion while being sandwiched in a press-contact state.

6. A microchip according to claim 1, further comprising:
a sample delivering portion which applies pressure to the sample in the sample-delivering reservoir so as to deliver the sample to the sample-delivered reservoir.

7. A microchip according to claim 1, wherein:
the sample-delivering reservoir comprises a plurality of sample-delivering reservoirs,
the channel comprises a plurality of different channels,
the sample comprises a plurality of samples affecting one another, the plurality of different channels being provided for the plurality of samples, respectively,
the first shutter portion comprises a plurality of first shutter portions,
the samples flow from the plurality of sample-delivering reservoirs into the sample-delivered reservoir, and
the plurality of first shutter portions are provided for the plurality of different channels, respectively.

8. A microchip according to claim 7, wherein the microchip is configured so that:
at an intersecting portion of the plurality of channels, one end of the first shutter portion is protruded into the intersecting portion; and
when one of the plurality of channels is opened by one of the first shutter portions at the intersecting portion so that the sample is delivered, another of the plurality of channels is closed by another of the first shutter portions.

9. A microchip according to claim 7, wherein at least one of the samples packed in the plurality of sample-delivering reservoirs comprises a cleaning liquid or a channel-stabilizing liquid.

\* \* \* \* \*